(12) United States Patent
Lopez Palacios et al.

(10) Patent No.: US 9,707,159 B2
(45) Date of Patent: Jul. 18, 2017

(54) BISGMA-FREE ORTHODONTIC ADHESIVES

(71) Applicant: UNIVERSIDAD NACIONAL AUTONOMA DE MEXICO, Distrito Federal (MX)

(72) Inventors: Eira Lopez Palacios, Distrito Federal (MX); Carlos Andres Alvarez Gayosso, Distrito Federal (MX); Gabriel Saez Espinola, Distrito Federal (MX)

(73) Assignee: UNIVERSIDAD NACIONAL AUTONOMA DE MEXICO, Distrito Federal (MX)

( * ) Notice: Subject to any disclaimer, the term of this patent is extended or adjusted under 35 U.S.C. 154(b) by 0 days.

(21) Appl. No.: 14/898,808

(22) PCT Filed: Jun. 17, 2014

(86) PCT No.: PCT/MX2014/000092
§ 371 (c)(1),
(2) Date: Dec. 16, 2015

(87) PCT Pub. No.: WO2014/204289
PCT Pub. Date: Dec. 24, 2014

(65) Prior Publication Data
US 2016/0120764 A1    May 5, 2016

(30) Foreign Application Priority Data

Jun. 17, 2013 (MX) .................... MX/a/2013/006893

(51) Int. Cl.
| | | |
|---|---|---|
| *C08F 2/46* | (2006.01) | |
| *C08F 2/50* | (2006.01) | |
| *C08G 61/04* | (2006.01) | |
| *A61K 6/00* | (2006.01) | |
| *A61L 24/02* | (2006.01) | |
| *A61L 24/06* | (2006.01) | |

(52) U.S. Cl.
CPC .......... *A61K 6/0023* (2013.01); *A61K 6/0008* (2013.01); *A61K 6/0029* (2013.01); *A61K 6/0088* (2013.01); *A61L 24/02* (2013.01); *A61L 24/06* (2013.01)

(58) Field of Classification Search
CPC .. A61K 6/0023; A61K 6/0088; A61K 6/0029; A61K 6/0008; A61L 24/06; A61L 24/02; C08L 33/06; C08L 33/10
USPC ................ 522/68, 6, 71, 189, 184, 1; 520/1
See application file for complete search history.

(56) References Cited

U.S. PATENT DOCUMENTS

| | | |
|---|---|---|
| 5,295,824 A | 3/1994 | Wong |
| 5,426,134 A | 6/1995 | Rheinberger et al. |
| 5,575,645 A | 11/1996 | Jacobs et al. |
| 5,810,584 A | 9/1998 | Wong |
| 6,090,867 A | 7/2000 | Starling, Jr. et al. |
| 7,963,769 B2 | 6/2011 | Qian |
| 2002/0082315 A1 | 6/2002 | Moszner et al. |

FOREIGN PATENT DOCUMENTS

WO    2007079070 A1    7/2007

OTHER PUBLICATIONS

International Search Report dated Oct. 13, 2014 for PCT/MX2014/000092.

*Primary Examiner* — Jessica E Whiteley
(74) *Attorney, Agent, or Firm* — Lucas & Mercanti, LLP

(57) ABSTRACT

Three adhesives formulated with Trimethylolpropane Trimethacrylate (TMPTMA) that do not contain BisGMA were developed, whereby the mutagenic and teratogenic risk by the release of bisphenol A is eliminated, and presented a better performance compared to the three commercial adhesives prepared with BisGMA (Adhesive A, Adhesive C and Adhesive B). The invention provides an adhesive used in one-step and provides a system which is formed by a primer and a slurry. The adhesives of the invention were compared with two commercial controls. They were physically characterized by assessing: hardening time, adhesion stress, elastic modulus, sorption and solubility at different pHs (6.8 and 7.7); by the obtained values premature detachments, white lesions below the appliance and microfiltration are avoided; its fluidity, film thickness were evaluated and were compared with those obtained from the three commercial adhesives. Storage stability and thermogravimetric analysis were assessed. The prepared adhesives with TMPTMA are photopolymerizables, thereby providing enough time to the operator to place the appliance in proper position, it is easy to handle, capable of supporting orthodontic biomechanics, has low elastic modulus, enables transitions of heavy arches reducing the risk of involuntary detachment of the appliances, have low viscosity, penetrates on both the brace retentions as those made with acid etching on enamel surface. Presenting adhesion to both the base of the attachments as well as to the enamel, its film thickness is minimal and does not alter the prescription system. When the appliance is removed at the end of the treatment, it does not cause structural damage to the enamel because the adhesive remains on the enamel and can be removed easily with a rotary instrument.

12 Claims, 18 Drawing Sheets

FIG. 4
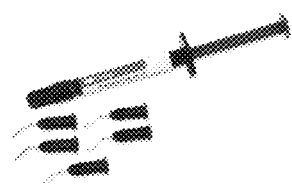

Mass loss of orthodontic adhesives subjected to heat TGA 5º C/min
TGA 25-60º C (5º C/min)

| Adhesive | Initial mass mg | Final mass mg | Mass loss mg | Mass loss percentage |
|---|---|---|---|---|
| 1 Step adhesive | 3.4 | 3.4 | 0 | 0 |
| Adhesive system | 2.02 | 2.017 | 0.003 | 0.1 |
| Transbond XT | 3.25 | 3.25 | 0 | 0 |
| Transbond LV | 1.97 | 1.97 | 0 | 0 |
| Enlight | 2.611 | 2.609 | 0.002 | 0.08 |

BISGMA-FREE ORTHODONTIC ADHESIVES

CROSS REFERENCE TO RELATED APPLICATION

This Application is a 371 of PCT/MX2014/000092 filed on Jun. 17, 2014 which, in turn, claimed the priority of Mexican Patent Application No. MX/a/2013/006893 filed on Jun. 17, 2013, both applications are incorporated herein by reference.

FIELD

The present invention lies in the field of attachments and reagents used for orthodontics, specifically to orthodontic adhesives, for instance, for braces.

BACKGROUND

Nowadays it is of common practice in dentistry the use of polymer coatings, for both sealant preventive purposes of pit and fissure (adhesives, etc.) and restorative (sealants), such as aesthetic purposes. In most of these materials, the polymerization (curing) process starts via a free radical mechanism, produced both chemically (self-curing systems) or by the action of light (light-cured systems). Despite progress in the development of new polymeric dental materials, there have been some problems in their application; including chemical degradation, mechanical damage of the polymer in the environment of the oral mucosa and allergic and toxicological problems.

Most photo-polymerizable dental coatings containing a mixture, carefully selected from mono- and multifunctional acrylic monomers, being one of the most used during the past years, 2-bis[p-(2-hydroxy-3-metacryloxypropoxy)phenyl]propane, commonly known as bisphenol A-glycidyl methacrylate (BisGMA), which was developed in 1956 by Rafael Bowen[1].

The BisGMA is mutagenic and carcinogenic, its chemical structure has two reactive links at both ends of the molecule. Studies show that DNA synthesis is affected in the presence of BisGMA at concentrations of 5 µmol per liter, in addition to exhibiting estrogenic actions. In cells, after contact with adhesives, as eventually occur during removal procedures of the appliances. There are also reports of allergic dermatitis in the dental field staff that has been attributed to the release of monomers of dental resins (composites)[2].

Bisphenol A plays an important role in almost all composites and sealants, and is the integral part of the molecule of BisGMA; Bisphenol A found in the mouth may originate from dental materials either to be used as direct ingredient, as a degradation product of other ingredients, such is the case of using bisphenol A dimethacrylate (BisDMA) (because this is exposed in oral cavity to the degradation of the esterases of the saliva); Bisphenol A found in the mouth may be caused to be present as trace material derived from the manufacture of other ingredients, such is the case of products containing BisGMA on sealants and adhesives compounds, because Bisphenol A is the precursor of BisGMA, so that residues may be present in the final product, this is very common if the reactions during manufacture are not adequately controlled.

In a 1996 study, detectable levels of Bisphenol A were reported in the saliva of patients treated with dental sealants (Nicolas Olea, et al. 1996)[4], in other studies (Fung, et al, 2000)[5] detectable levels are shown to be below reported levels by Olea. The short-term administration of BisGMA and/or bisphenol A in animals or cell cultures can induce changes in estrogen-sensitive organs or cells, however, considering the doses and routes of administration could conclude that the estrogenic effects when using dental composites containing or based on BisGMA is insignificant, and some studies have shown that Bisphenol A is not hydrolysed by BisGMA and have not found significant amounts of BISPHENOL A in dental sealants or composites; Notwithstanding the foregoing, studies are needed to evaluate the long-term effects, taking into consideration that the orthodontist are systematically exposed to these compounds and that users of orthodontic appliances (braces, bonded lingual retainers, etc.) maintain contact with these materials for an average of two years, the duration of treatment. The current trend is to minimize human exposure to Bisphenol A in dental materials as a health precaution[6,7].

Furthermore, the BisGMA is a monomer having a high molecular weight, and by their stereotactic structure and high viscosity, presents a phenomenon of steric hindrance during the polymerization, and resulted in a rigid and inflexible material obtained to move the space, this makes it difficult to handle, so that it should add another monomer such as triethylene glycol dimethacrylate (TEGDMA) to dilute its hard consistency and provide better performance.

With respect to the types of adhesives developed for improving the performance or facilitate some of the orthodontic procedures, they can be found in the following patent documents:

The U.S. Pat. No. 6,090,867 relates to a dental adhesive system that allows easy removal of ceramic braces from the adhesive enamel surface based on acrylate comprising a plasticizer which gives ductility, and wherein the plasticizer has poor solubility in water or saliva, it does not evaporate at the temperature of the oral cavity and is not toxic at the doses used.

The U.S. Pat. No. 5,575,645 relates to an orthodontic appliance placed on a container and contains a stable adhesive to be stored, comprising EBDA and is free of TEGDMA. The EBDA may contain EBDMA, and after polymerize has a bond strength of 25 to 54 kg/cm$^2$ has a consistency of 12 to 24.5 mm.

The U.S. Pat. No. 5,295,824 relates to a plastic brace (polycarbonate) with a first layer (monomeric acrylic adhesive) adhered to the surface that makes contact with the tooth and its function is to increase the bond strength between the brace and the dental adhesive; to obtain this type of auto-adhesive brace, it is required applied to the brace a solvating mixture and heated to a temperature of 60 to 100° C. to volatilize the solvents, and that the monomers and with the solvation mixture conform to the primer, and requires 2-30 minutes to diffuse to the surface of the brace that will make contact with the tooth, it can only ensure the stability of the brace during the first few weeks, so this method besides being laborious inefficient.

The U.S. Pat. No. 5,810,584 refers to a brace that carries the pre-applied adhesive on the bonding surface, and is characterized by not being sticky, it mentions formulations of these adhesives, all of these adhesives are based on BisGMA.

Adobes-Martin has reported the effectiveness of self-etching adhesives in the cementing braces. The self-etching adhesives are an alternative for orthodontic cemented, these substances are a weak acid incorporated to the primer, that is why they call it of "one-step", and the number of procedures is reduced. These products combine the conditioner of the enamel along with the hydrophilic adhesive system in a single vial, allowing simplify the first 2 steps of the braces cementation (etching with orthophosphoric acid followed by the application of bonding resin) and transforming them into a single gesture, the bond strength of these adhesives should be optimal, but no results are provided nor other data reported of parameters expected for a good performance in other aspects of its functions[9].

There is another procedure where etchant acid is rubbed and must be washed and dried; then it applied to a primer, which is photopolymerized for 5 to 10 seconds depending on the manufacturer; after the adhesive is applied to the brace, it is positioned on the enamel and polymerized for 10 to 15 seconds. With our experimental one-step adhesive, the step that is removed is the first application; i.e., the etchant acid is rubbed over the tooth (phosphoric acid 37%), washed and dried; the adhesive is placed on the brace and this is placed on the tooth and polimerized for 10 seconds. We are eliminating a polymer layer (the primer) to which is going to adhere the polymer that was placed in the brace, so that the adhesive will polimerized within retentions created in the enamel surface by the acid etching.

The thesis entitled "Valoración física de una resina compuesta a base de Trimetilolpropano trimetacrilato" (Student: Montiel Millan, December 2010 Tutors: Sáez Espínola G. López Palacios E.), aimed to evaluate the physical performance of an experimental resin for reconstruction, based on Trimethylacrilate Trimethylolpropane; however, by the results in the conclusions it is stated that a polymer with adequate performance for the reconstruction of teeth subjected to masticatory loads are not obtained, it was concluded that the silver formulation did not have the desired performance, so changes were needed and again experimental evaluations.

The work presented in "Congreso intede la IADR división mexicana" held in May 2013 entitled "Effect of bi, tri and penta functional monomers on bond strength of denture base resin to acrylic teeth" (Student: Reséndiz Melgar H., Tutor Barceló Santana, F: H. Advisor Álvarez Gayosso C.) aimed to evaluate the stress of base denture adhesion of PMMA (polymethylmethacrylate) and experimental adhesives prepared with monomers bi, tri or multifunctional. It was concluded that resistance is comparable with commercial adhesives of the denture-teeth type of PMMA.

By consequence of this, it has been sought to omit the drawbacks of adhesives, primers and systems of the prior art, by developing a BisGMA-free orthodontic adhesive that is used in one-step and provides a system that is formed by a primer and slurry. The use of adhesives of the present invention is easy handling and further shows adhesion to both the base of the attachment and the enamel.

OBJECTS OF THE INVENTION

Given the shortcomings of the prior art, an object of the present invention to provide an orthodontic adhesive on paste formulated with Trimethylolpropane Trimethacrylate not containing BisGMA, eliminating the mutagenic and teratogenic risk A further object of the present invention is to provide an orthodontic adhesive with an elastic modulus which allows proper transmission of generated forces by orthodontic appliances to the tooth.

It is an object of the present invention to provide an orthodontic adhesive with adhesion to both the base of the attachment as well as to the enamel so not damage the enamel.

It is an object of the present invention to provide an orthodontic adhesive with minimal sorption and solubility.

It is another object of the present invention to provide an orthodontic adhesive to penetrate easily in both the microdowns created on the enamel by acid etching effect, and the base of the attachments.

It is still another object of the present invention to provide an orthodontic adhesive with an adhesion force that supports the tensile and torsional forces of the movements generated by orthodontic appliances.

It is a further object of the present invention to provide a stable orthodontic adhesive at rest and temperature changes.

It is another object of the present invention to provide an orthodontic adhesive that is used in one-step and provides a system that is formed by a primer and slurry.

Yet another object of the invention to provide an adhesive with a film thickness of $39\pm2$ μm which is suitable to enable a better performance of motion of the braces on the teeth.

Another object of the invention is to provide an adhesive system comprising a primer and a slurry 1 both formed by two phases, organic and inorganic.

BRIEF DESCRIPTION OF THE DRAWINGS

The novel features that are considered characteristic of the present invention are set forth with particularity in the appended claims. However, the invention itself, both its structural organization, together with further objects and advantages thereof, will be better understood from the following detailed description of certain preferred embodiments when read in connection with the accompanying drawings, in which:

FIG. 4 shows a photograph of Adhesive A, Adhesive on paste Transbond XT.

FIG. 5 shows a photograph of the Adhesive C, Adhesive on paste Transbond LV.

FIG. 6 shows a photograph of the preferred kit comprising: etchant acid (strong acid), a first and a paste adhesive.

DETAILED DESCRIPTION

Figure 1:
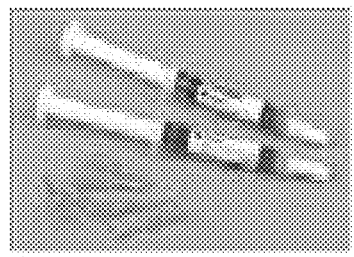
FIG. 1 shows a photograph of the etchant acid, strong acid that may be orthophosphoric or phosphoric acid 35% to exercise the demineralizing action on tooth enamel.

Referring to the accompanying drawings, the present invention provides to the field of orthodontics adhesives and adhesive systems for devices or attachments that adhere to the teeth, it is because of the development of a dental adhesive to cement adhesives as braces, buttons and pipes either metal or plastic to dental enamel to perform orthodontic treatment and also includes the formulation of a primer and a slurry which function as a system. There are three adhesive compositions characterized by being safe from enamel abuse of the teeth and also for being BisGMA-free, so they are less toxic.

The present invention was derived from the development of an adhesive material with orthodontic application substituting the Bisphenol A-glycidyl methacrylate (BisGMA) by a multifunctional methacrylate, Trimethylolpropane Trimethacrylate (TMPTMA); also known as: 1,1,1-trimethylolpropane trimethacrylate; 1,3-Propanediol, 2-ethyl-2-(hydroxymethyl)-trimethacrylate; 2-ethyl-2(hydroxymetil)-1,3-propanediol trimethacrylate; ATM 11; Acriester TMP; Blemmer PTT; methacrylic acid, 1,1,1-trihydroxymethyl propane triester; TMPT (crosslinking agent); 2-propenoic acid, 2-methyl, 1,1'-(2-ethyl-2-(((2-methyl-1-oxo-2-propen-1-yl)oxy)methyl)-1,3-propanediil)ester; 2-propenoic acid, 2-methyl-,2-ethyl-2-(((2-methyl-1-oxo-2-propenyl)oxy) methyl)-1,3-propanediyl ester; methacrylic acid, triester with 2-ethyl-2-(hydroxymethyl)-1,3-propanediol.

Denture adhesives of the invention were tested experimentally and were compared with three existing in the market, as detailed below. The adhesives of the invention showed the following characteristics:

Its formulation is free of BisGMA, which is an important advantage since this monomer, as already mentioned, has shown to be mutagenic and have estrogenic effects on the release of Bisphenol A, in salivary well.

The adhesives of the invention have been tested experimentally and it was found that are capable of supporting orthodontic biomechanics, i.e., supporting the tensile and torsional forces with low elastic modulus.

The adhesives of the invention are low viscosity adhesives which penetrate both the retentions of the brace as those made by acid etching in the enamel surface. Exhibit adhesion to both the base of the attachments as well as to the enamel.

The adhesives of the invention are photopolymerizables, meaning that the operator will have enough time to put the appliance in proper position and adhesives are easy to handle. Its film thickness is minimal and does not alter the prescription system.

The adhesives of the invention have little or no sorption, also have little or no solubility to avoid premature detachment, to avoid white lesions below the appliance and to avoid microfiltration; therefore, when removing the appliance at the end of treatment does not cause damage to the structural enamel.

The adhesives of the invention may remain in the mouth long enough of the current orthodontic treatments of straight wire, which has been estimated at an average of 24 months. The adhesives of the invention are two different formulations:

The first of the adhesives will be named hereinafter "one-step" because it is formed by a slurry (slurry 1) which consists of two phases:

A. organic phase: (Monomer: Trimethylolpropane trimethacrylate 40.67% w/w (TMPTMA), Photoinitiator: camphoroquinone 0.3%, Accelerator: Dimethyl p-toluidine 0.03%) and B. inorganic phase: silanized silicon dioxide of nanometer particle size (16 nm) 2% to 57% w/w of silanized silicon dioxide of micron particle size (325 microns) dioxide.

With this adhesive called "one-step" a step in the procedures for attaching braces is removed and also a single adhesive phase is provided and not two polymerized layers as in the case of self-etching primers and in conventional systems, the latter is particularly important because having an adhesive layer with low elastic modulus allows that after the brace is detached, the fault is present in the adhesive, i.e. the adhesive polymerized within the retentions to remain there and the fracture being in the body of the adhesive; so that they will have to remove the remaining adhesive on the enamel surface with a rotary tool to ensure the integrity of the enamel rods; commercial adhesives such as Transbond LV and Enlight after detaching the braces, do not show adhesive residue on the enamel but this can be can lead to the release of enamel rods resulting in pain for the patient and the need of surface repair dental to achieve aesthetics again. With the one-step adhesive of the invention, the use of instruments to repair the damage caused to the enamel is avoided and only rotary instruments are used to remove debris left in the enamel, in which case it is recommended the rotary tool of tungsten at low speed.

The second of the adhesives will be named hereinafter as "adhesive system" because two adhesives act together and for their use is required applying a first layer called "Primer" followed by a layer of a slurry (slurry 2).

The primer consists of two phases:
1. Organic phase: Monomer: Trimethylolpropane trimethacrylate 83.67% w/w, Solvent: isopropyl alcohol 10%, Photoinitiator: Camphoroquinone 0.3%, Accelerator: Dimethyl p-toluidine 0.03%.
2. Inorganic phase: silanized silicon dioxide of nanometer particle size (16 nm) 6%.

The slurry 2 is formed by two phases:
1. Organic phase: Monomer: Trimethylolpropane trimethacrylate 40.67% w/w, Photoinitiator: Camphoroquinone 0.3%, Accelerator: Dimethyl p-toluidine 0.03%.
2. Inorganic phase: silanized silicon dioxide of nanometer particle size (16 nm) 3% and 56% of silanized silicon dioxide of micron particle size (325 μm).

As hereinafter described, for the development and evaluation of the adhesives of the invention, were performed thermal testing of 20 to 60° C., as the oral cavity can withstand temperatures of 5 to 55° C., i.e. when the patient consumes cold things as ice cream or as hot coffee. Results where no mass loss at these temperatures are shown. Sorption and solubility tests were also carried out, and were performed to assess the resins with filler for reconstruction, which are exposed to saliva in the mouth; the studies were made in water immersion at different pH to simulate the saliva of patients with much caries (pH 6.8) and to simulate patients with braces that have come to develop a periodontal disease who have shown a more basic pH (pH 7.7) where results show minimal solubility.

In Example 1, the procedure for its preparation is described. The mixture used for all experimental part was prepared by a single operator (to minimize errors due to manipulation) and was stored under controlled humidity and temperature (65±2%, 21±2° C.). The reagents were kept for 24 hours at 65±2% HR. and 21±2° C. before use.

The TMPTMA is a monomer having high reactivity and low viscosity (45 mPa at 25° C.), gives the adhesive of the invention, its characteristics, as could be demonstrated in the experimental development and finally two competitive products obtained in the market, as the adhesive one-step has better performance than any of the three commercial adhesives prepared with Bis A-glycidyl methacrylate (BisGMA), with which it was compared, and the second shows the suggested performance for proposed parameters by Reynolds[10], for orthodontic adhesives parameters to avoid damage to the tooth structure and also better physical properties than commercial compared with it.

To determine which commercial adhesives would be used as a comparative survey with some educational institutions of orthodontic specialty in Mexico (state and private) was performed, to determine which were most used in the country[11]. They were selected as comparative three different commercial adhesives:

A. Adhesive system, Transbond XT™[12] (FIG. 4) (Light Cure Adhesive Paste 3M Unitek. Monrovia, Calif.), hereinafter "adhesive A". (Consisting of first "Transbond" and paste Transbond XT).

Figure 2:
FIG. 2 shows a photograph of the Primer Transbond.

The procedure of use comprises: applying the self-etching Transbond primer (FIG. 3), and 2) applying the Transbond XT paste (FIG. 4); or 1), applying the etchant acid to the tooth (FIG. 1), 2) applying Transbond primer (FIG. 2) and applying the Transbond XT paste (FIG. 4).

B. Adhesive system, Enlight™[13] (FIG. 9) (light cure adhesive. Ormco. Glendora, Calif.), hereinafter "adhesive B" (constituted by a primer "Ortho Solo" and paste "Enlight").

Figure 7:
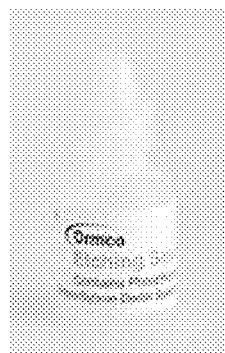
FIG. 7 shows a photograph of the etchant acid (strong acid)
Figure 8:
FIG. 8 shows a photograph of Orto Solo™ primer.
Figure 9:
FIG. 9 shows a photograph of the Adhesive B, Adhesive on paste Enlight.

The procedure of use comprises: 1) applying an etchant acid (FIG. 7), 2) applying the Orto Solo™ primer (FIGS. 8 and 3) applying the Enlight™ paste (FIG. 9). FIG. 6 shows the kit of ORMCO™, which includes elements of FIGS. 7, 8 and 9.

Because another objective was to produce an adhesive of low viscosity, also took as parameter the following:

C. Adhesive system of Transbond Supreme LV™ of Low Viscosity[12] (FIG. 5) (Light Cure Adhesive 3M Unitek, Monrovia, Calif.), or, hereinafter "adhesive C" (constituted by a "Transbond" auto-etching primer and paste Transbond LV).

The procedure of use comprises: 1) applying the first Transbond auto-etching (FIG. 3) and 2) applying the Transbond LV paste (FIG. 5); or 1) applying to the tooth the etchant acid (FIG. 1), 2) applying the Transbond primer (FIG. 2) and apply the Transbond LV paste (FIG. 5).

The adhesive of one-step of the invention unlike commercial ones (FIGS. 1-9), does not require prior application of a primary reagent hereinafter referred as Primer; the latter is applied immediately after performing the etching acid on the enamel surface. The absence of this step leads to characterize the adhesive of the invention as a "one-step" adhesive, although this feature refers to the process when it is used to attach braces. With the invention, the possibility of decreasing in time and form the placement of braces is provided (adhesion or bonding of the brace to the tooth) since conventional methods require application of two products after the required acid etching.

The adhesive of one-step of the invention has a cure time of 10 seconds that is the lowest so far achieved and is similar to commercial: A and C that also require 10 seconds to cure and is less than the commercial adhesive B, which needs 15 seconds. The big advantage is the total time from application of the primer to complete the photopolymerization, since while commercial products need 15 to 20 seconds in total because it is necessary to apply primer (5 seconds) and photopolymerize for 10 additional seconds, the adhesive of the invention requires only 10 seconds in total for not requiring primer.

Example 2 teaches how the consumed curing time on each tooth was measured (FIG. 10), graph 1 (FIG. 11) shows the curing time of the adhesives of the invention. In graph 2 (FIG. 12) is shown the total time that it would take using each adhesive on average: the adhesive B (Enlight) needs 20 seconds to apply its entire system including primer (5 s) and paste (15 s); both Transbond LV (adhesive C) and Transbond XT (adhesive A) required 15 seconds for all their system: Primer (5 s) and paste (10 s); the "one-step" adhesive, object of this invention requires only 10 seconds to be applied and the adhesive system requires 15 seconds in total, such as adhesives A and C. It should be considered that in medical practice, the consumed time in the development and placement of instruments and appliances turns out to be an aspect that adds value to the products being used.

Figure 3:
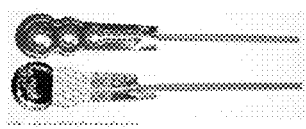
FIG. 3 shows a photograph of the Primer Transbond, being a kit that is constituted of a weak acid that can be acrylic or citric and separately a primer that are mixed until used.

Regarding the self-etching Transbond primer as shown in FIG. 3, this allows the application of the adhesive in paste in two steps only, since the primer is already included; however, its use comprises making the mixture of primer and acid just before applying the adhesive paste, so the procedure is complicated and time consuming, which in practice is relevant. Also generates a film whose thickness adds to the thickness of the adhesive paste resulting in a film thickness similar to which is formed using the system employing acid, then the primer and finally the adhesive paste, as has been described when using Adhesives A, B and C.

The adhesive of one-step of the invention was tested and compared with commercial adhesives A, B and C as to the parameter of adhesion strength, considering international standards[14], with substrate of human dental enamel and Metal attachments (braces) and presented 9.5±1.5 MPa without placing a primer. This resistance is similar to that one presented by commercial adhesives: Adhesive A: (9.4±0.8 MPa) Adhesive C: (9.5±2.0 MPa) and adhesive B (10.0±2.4 MPa) that need to the primer to achieve adhesion.

The elastic modulus which provided the adhesive of the invention (experimental) was 30 MPa, this is significantly lower than commercial ones: A (44 MPa), C (45 MPa) and B (52 MPa). The advantage of a low elastic modulus is that when a more elastic material will allow that when the brace receives a force, the adhesive dissipate such force and transmit it to the tooth to achieve tooth movement without failure.

Regarding the results on the site and type of failure of the adhesives[15], it was found that at the time of the brace detachment, both the adhesive object of this invention and the adhesive A remain adhered to the enamel. This ensures the integrity of the enamel rods avoiding detaching them at moment of removing the appliances at the end of treatment. The other adhesives (A, B and C) left traces on the enamel but also on the screen of the brace indicating that could be damage to the enamel with which the treatment is compromised because now is necessary to restore the enamel. Adhesive C less than 50% of adhesive on the enamel and adhesive B showed more than 50% of adhesive on the tooth.

The fluidity of the adhesive of the invention[16,17] was 330 mm$^2$, which allowed that easily penetrate both micro retentions created on enamel by acid etching effect and in the base of the adhesives. Whereas commercial adhesives not exceed 300 mm$^2$, i.e. they are more viscous either by the leading ingredients or because they are prepared with inorganic fillers in a higher percentage than the adhesive of the invention (experimental).

There are reports in the literature of patients with orthodontic appliances and alterations in the oral health that present different salivary pH ranging from 5.5 to 7.8[18-19]; within the relevant quality of the adhesive of the invention, the effect of oral pH in the sorption phenomena and solubility was determined, as these are also parameters indicating the quality of dental materials. The water sorption is a diffusion controlled process within the resin matrix, in the case of the adhesive, which may cause its degradation and breaking to the bond between the filler and the matrix, also can cause the release of material particles, ions and residual monomers, phenomenon identified as solubility, causing a decrease in weight and size in the materials, which can affect its mechanical properties and cause color changes[20].

Sorption and solubility presented by the adhesive of the invention, when tested at pH7[29], was similar to two commercial adhesives (Adhesive A and Adhesive C) and less than adhesive B EXP (300 µg/mm$^3$, 300 µg/mm$^3$), Adhesive A (300 µg/mm$^3$, 300 µg/mm$^3$), Adhesive C (289 µg/mm$^3$, 318 µg/mm$^3$) and Adhesive B (330 µg/mm$^2$, 389 µg/mm$^2$). When the adhesives were tested at pH 6.8[29], the adhesive of the invention showed lower sorption than the commercial ones: (294 µg/mm$^3$ and 294 µg/mm$^3$), the adhesive A (300 µg/mm$^2$, 391 µg/mm$^2$), the adhesive C (318 µg/mm$^2$, 311 µg/mm$^2$) and the adhesive B (389 µg/mm$^2$, 402 µg/mm$^3$), with which it can be inferred that the adhesive of the invention is more resistant to acid medium and in patients with salivary pH more acidic (high caries rate) the adhesive of the invention is more stable than commercial ones, those with higher sorption and greater solubility.

However, as there is greater separation between the brace and the tooth surface, which is measured as film thickness[29], the possibility of uncontrolled dental movements is open. The adhesive of the invention showed a film thickness of 39±2 µm lower than the behavior of Adhesive C (47±2 µm) and with respect to other commercial adhesives A and B, showed film thicknesses in different film thickness much more marked: Adhesive A (69±1 µm) and Adhesive B (124±1 µm); so it is inferred that its use might compromise the treatment in the absence of the necessary control of tooth movement.

The shelf life is another parameter that was measured. Experimental adhesive of the invention has shown to be stable to stand at 21±1° C., it has not presented phase separation nor apparent change in color.

Stability in oral temperatures is another parameter that was measured: the oral cavity is subject to temperature changes due to intake of food and beverages, this temperature ranges from 5 to 55° C. Experimental adhesive of the invention, like the three commercial adhesives tested were showed stability when heated to room temperature (25° C.) to 60° C. since no mass loss introduced.

Figure 15:
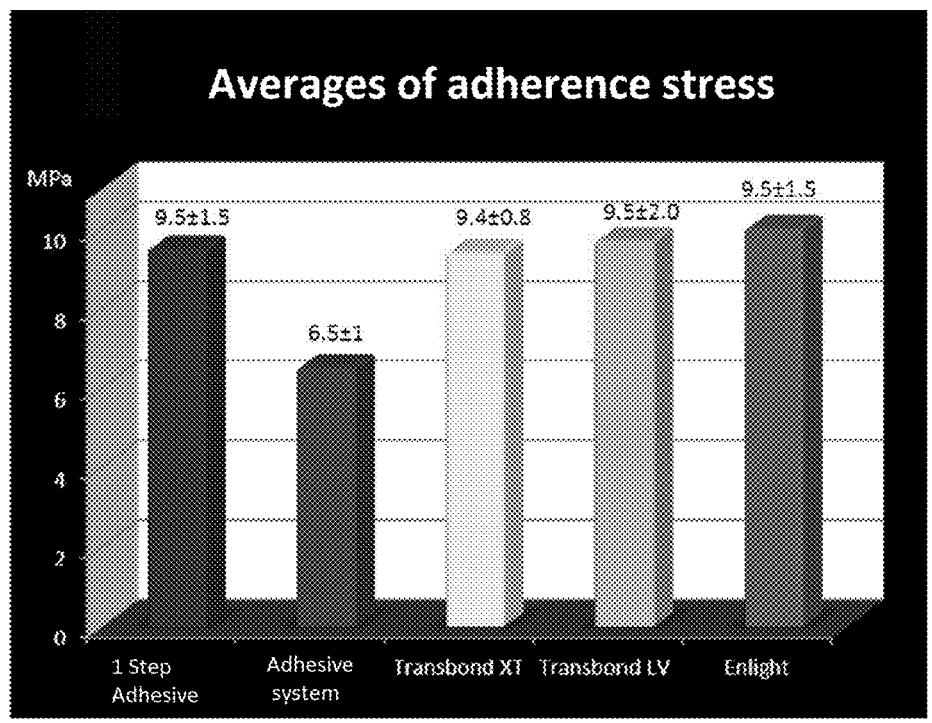
FIG. 15 is a graph showing the average adherence stress of orthodontic adhesives.

Regarding the adhesive system including a primer and a slurry, these two different formulations which give completely different values, not higher than commercial ones. The bonding system presents less adhesion stress than commercial ones but within the parameters mentioned by Reynolds[10] to support orthodontic biomechanics without damaging the enamel rods and with different characteristics in terms of sorption, solubility, fluidity, film thickness (FIG. 15). Unlike the first adhesive of the invention referred to as one-step, the adhesive system of the invention as well as commercial systems (FIG. 1-9) requires the prior application of a primary called primer; the latter is applied immediately after performing the etching on the enamel surface.

The adhesive system of the invention presents hardening time similar to the commercial ones: Transbond XT and Transbond LV, require 10 seconds to harden and less than Enlight, that need 15 seconds. The total time from application of the primer to complete the polymerization, is like the commercial ones Transbond XT and Transbond LV (15 s), Enlight requires 20 seconds.

The adhesive system of the invention when tested with human tooth enamel substrate and metallic attachments (braces) presented 6.5±1 MPa of resistance, this resistance is lower than that presented by the commercial adhesives: Transbond XT (9.4±0.8 MPa), Transbond LV: (9.5±1.5 MPa) and Enlight (9.5±1.5 MPa). The advantage of the experimental adhesive system is that by presenting sufficient adhesion to withstand the biomechanical orthodontic, but not too much so as commercial ones, reduces the risk to cause detachment of enamel rods when removing the appliance.

Figure 16:
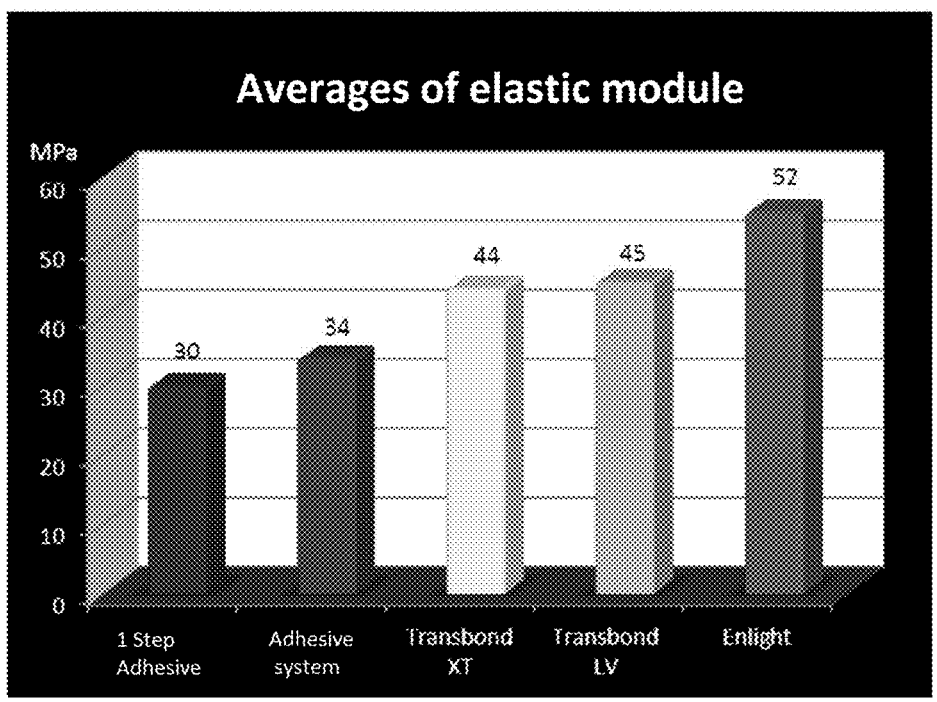
FIG. 16 is a graph showing the average elastic modulus of orthodontic adhesives.

The elastic modulus which provided the adhesive system of the invention was significantly lower than commercial ones, 34 MPa; Transbond XT (44 MPa), Transbond LV (45 MPa) and Enlight (55 MPa). The advantage of a low elastic modulus is that being a more elastic material will allow that when the brace receives a force, the adhesive: dissipates and transmits such force to the tooth to achieve tooth movement without failure (FIG. 16).

Upon detachment of the brace, both the adhesive system of the invention as Transbond XT stick to the enamel. This ensures the integrity of the enamel rods avoiding detaching when removing the appliance at the end of treatment. The other adhesives left residues on the enamel and on the brace mesh indicating that there could be damage to the enamel with which the treatment is compromised because now is necessary to restore the enamel. Adhesive C less than 50% of adhesive on the enamel and Enlight showed more than 50% of adhesive on the. The fluidity of the adhesive system of the invention:

1. The Prime has a fluidity of 330 mm$^2$, this allows that easily penetrate in the microretentions created on the enamel by acid etching effect. While commercial Transbond XT presented 353=$^2$, at the time of being more fluid it could have better penetration, and in case of trying to use this primer in dentine can be more irritating to the pulp: Ortho solo presented 207 mm$^2$, this means that it is more viscous either by the ingredients that contain or because are prepared with inorganic fillers at a higher rate than the experimental primer.

2. The slurry has a fluidity of 348 mm$^2$, this allows that easily penetrate in the base of the attachments. Whereas commercial ones do not exceed 300 mm$^2$, i.e. they are more viscous either by the ingredients that contain or leading ingredients or because are prepared with inorganic fillers at a higher rate than the experimental adhesive.

Sorption and solubility that provided the adhesive system of the invention:

A. The primer: When tested at pH 7.7[18], was similar to the commercial Transbond XT EXP (0.04 µg/mm$^3$, −0.07 µg/mm$^3$) and Transbond XT (0.05 µg/mm$^3$, −0.08 µg/mm$^3$) behavior completely different from commercial Ortho Solo (−0.03 µg/mm$^3$, 0.25 µg/mm$^3$). When the adhesives were tested at pH 6.8, the experimental adhesive (0.06 µg/mm$^3$, 0.06 µg/mm$^3$) showed higher sorption than the commercial: Transbond XT (0.03 µg/mm$^3$, 0.04 µg/mm$^3$) and less than commercial Ortho Solo (0.03 µg/mm$^3$, 0.1 µg/mm$^3$), with which it can be inferred that the experimental adhesive is more resistant to acid medium and in patients with salivary pH more acidic (with high rates of caries).

B. Slurry: When tested at pH 7.7, it was lower than commercial ones (Transbond XT and Transbond LV) and less than Experimental Enlight (300 µg/mm$^3$, 288 µg/mm$^3$), Transbond XT (300 µg/mm$^3$, 300 µg/mm$^3$), Transbond LV (289 µg/mm$^3$, 318 µg/mm$^3$) and Enlight (330 µg/mm$^3$, 389 µg/mm$^3$). When the adhesives were tested at pH 6.8[32], the experimental adhesive (300 µg/mm$^3$, 288 µg/mm$^3$) showed lower sorption than commercials: Transbond XT (300 µg/mm$^3$, 391 µg/mm$^3$), Transbond LV (318 µg/mm$^3$, 311 µg/mm$^3$) and Enlight (389 µg/mm$^3$, 402 µg/mm$^3$), with which it can be inferred that the experimental adhesive is more resistant to acid medium and in patients with salivary pH more acid (high caries rate), the experimental one is more stable than commercial, those with higher sorption and greater solubility.

As there is greater separation between the brace and the tooth surface, the possibility of uncontrolled dental movements is open. The adhesive system of the invention: (paste) presented a film thickness of 26±1 µm much lower than Transbond LV (47±2 µm), Transbond XT (69±1 µm) and Enlight (124±1 µm) by it is inferred that use them might compromise treatment in the absence of such control of tooth movement.

Figure 32:
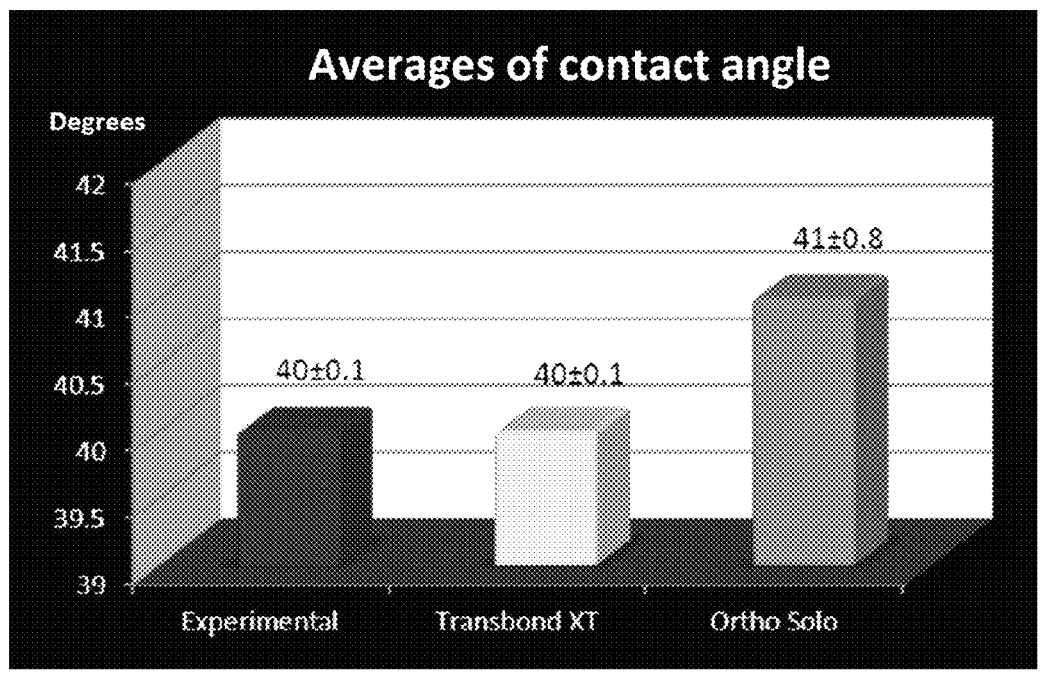
FIG. 32 is a graph showing the average contact angle of the adhesive systems primers.

At a lower contact angle[32], the primer has a higher wetting area with the substrate and better penetration in microretentions created by the acid etching. The first system of the invention had the same contact angle value of the commercial Transbond XT (40±0.1 degrees); slightly lower than that presented by commercial Ortho only, included in the system of adhesion of the commercial Enlight (41±0.8 degrees); (FIG. 32).

Figure 33:
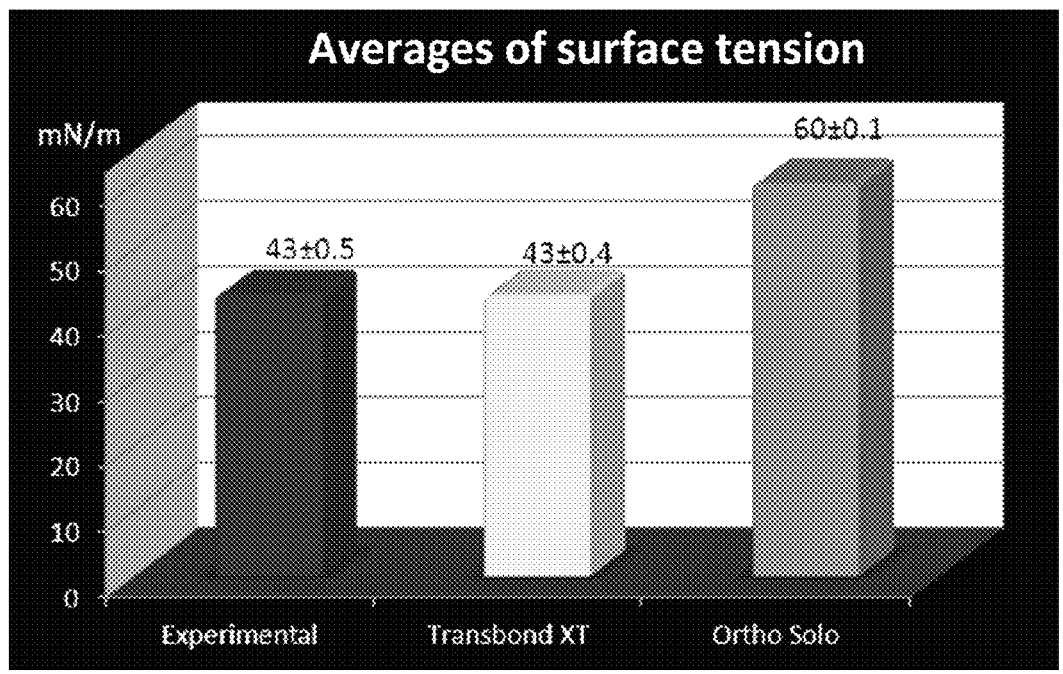
FIG. 33 is a graph showing the average surface tension of the primer adhesive system.

Surface tension[33] allows that the primer with lower values together with the contact angle and fluidity, presents a greater adhesion area and penetrate to the microretentions created in the enamel surface by etching action. The first experimental had lower values (40±0.5 mN/m) than the two commercial primers Transbond XT (43±0.4 mN/m) and Ortho Solo (60±0.1 mN/m), (FIG. 33).

It is important to note that has not been found written evidence containing information on the use of TMPTMA as a sole monomer to prepare adhesives or primers for orthodontics or other dental adhesive.

The object of the invention is to provide to the technical field an adhesive whose organic phase is basically formed by the monomer TMPTMA (40.00-50.00% w/w), and has Camphoroquinone (from 0.10 to 0.50%, preferably 0.3% (w/w)) as photoinitiator, and dimethyl p-toluidine (0.01-0.05%, preferably 0.03%) as accelerator, and whose inorganic phase is constituted by silanized silicon dioxide with micrometric particle size (16 nm) (at 1.00 to 2.00% preferably 2%) and silanized silicon dioxide with micron particle size (325 µm) (from 50.00 to 60.00%, preferably 57%, relative to the total weight).

The object of the invention is to provide to the technical field an adhesive that due to can be used in a single step, enhance the procedure of placing the braces, so it is an adhesive that provides a competitive advantage in the market, which decreases the cost and chair time with the patient, additionally, is a relevant feature that does not contain BisGMA in its formulation.

Another object of the invention is to provide an adhesive for orthodontic applications and for dental purposes generally, having numerous not only desirable features in an adhesive of its type, but exceeds several of the features, consists of a single monomer, so that does not presents copolymerization and wherein said monomer is a methacrylate with three functional groups, which by type of polymerization that presents allows having an elastic modulus lower than those of known adhesives, which results in optimal performance for orthodontics, particularly of the functions of the braces; It has minimal sorption and solubility, this helps to its stability under different pH conditions, so that will be stable regardless of the patient salivary pH. A further object of the invention is to provide an acidic medium resistant adhesive suitable for patients presenting even more acidic salivary pH (because of high levels of caries) the adhesive of the invention is finally more stable than commercial ones, those with higher sorption and higher solubility.

An embodiment of the invention is to formulate the adhesive of the invention so that it can be used as: cement to orthodontic bands, cementing and cementation of veneers and cementation of Maryland prosthesis (bridges). Any adjustments in such formulations may be concretized by a person with medium knowledge in the technical field.

One embodiment of the invention comprises independently provide a slurry 1, whose organic phase is comprised of: a monomer: Trimethylolpropane trimethacrylate 40.67% w/w, Photoinitiator: Camphoroquinone 0.3%, Accelerator: Dimethyl p-toluidine 0.03%, the inorganic phase of the slurry 1 is from: silanized silicon dioxide with nanometer particle size (16 nm) 2% and 56% of silanized silicon dioxide with micron particle size (325 microns).

One embodiment of the invention comprises providing an orthodontic primer independently characterized by having two phases: An organic phase comprising: monomer trimethylolpropane trimethacrylate 83.67% w/w; Solvent: isopropyl alcohol 10%; Photoinitiator: Camphoroquinone 0.3%; Accelerator: Dimethyl-p-toluidine 0.03%. The inorganic phase of the primer is constituted by silanized silicon dioxide with nanometer particle size (16 nm) 6%.

Because TMPTMA attacks some plastics, be advisable to store and dispense the three types of adhesives in amber vitreous syringes to isolate them of light, these syringes having a metal nozzle for dispensing the adhesive directly onto the base of the braces and adhesives.

It is an important feature of the invention, featuring an adhesive which is adhered to tooth enamel once removed from the brace, whereby the integrity of the tooth enamel is guaranteed. An additional advantage is that because of its fluidity 330 mm$^2$, the adhesive penetrates more easily to micro-downs generated by the etching.

One embodiment of the invention is to provide the adhesive of the invention formulated in an amber vitreous syringes with disposable dispensing nozzles because the etching can be performed with any etchant acid that has the orthodontist.

Another embodiment of the invention is to provide a kit or equipment comprising the liquid etchant acid into a dropper bottle; the adhesive of the invention formulated in an amber vitreous syringes with disposable dispensing nozzles.

Another embodiment of the invention provides a kit or equipment comprising the liquid etchant acid, the primer in an amber vitreous bottle with dropper and the adhesive paste of the invention in amber glass syringe with dispensing nozzle for its application.

Another embodiment of the invention is to provide a kit comprising the slurry of the invention and a primer of the invention, both independently packaged and protected from light.

One embodiment of the invention is to provide an aesthetic orthodontic treatment method comprising applying the primer and the slurry of the invention for adjusting orthodontic appliances, including braces.

One embodiment of the invention is to provide an aesthetic orthodontic treatment method of applying the adhesive in one-step of the invention for adjusting orthodontic appliances, including braces.

The present invention will be better understood from the following examples, which are presented for illustrative purposes to enable understanding of the preferred embodiments of the present invention, without thereby is implied that there are no other forms not illustrated they can be implemented based on the detailed description above performed.

The following examples are illustrative of how to obtain and use the invention and distinguish their performance and are presented without intending to limit the scope of the invention.

EXAMPLES

Example 1: Process for Obtaining the Adhesives

Adhesive for One-Step:
Monomer trimethylolpropane trimethacrylate (TMPTMA) 40.67% (w/w) with initiator camphoroquinone 0.3% were mixed. When viewing a homogeneous mixture the photo-activator Dimethyl p-toluidine 0.03% was added, then, the nanometric silicon dioxide (325 microns) up 57%, to finish with nanometric silicon dioxide (16 nm) 2%. After obtaining a homogeneous mixture, it was stored in an amber bottle, labeled with the number and date of the mixture preparation. The mixtures were made into a chamber illuminated with security light to prevent polymerization.

Adhesive System:
a) Primer: the monomer was mixed with the accelerator (later the solvent (10% isopropyl alcohol) was added, mixing in a closed vessel to avoid evaporation. When viewing a homogeneous mixture, the photoactivator (camphoroquinone 0.3%) was added. Then the silicon dioxide (silanized silicon dioxide with nanometer particle size (16 nm) 6% silicon) was added. After obtaining a homogeneous mixture, was stored in an amber bottle, labeled with the number of mixing and production date.

b) Slurry: the monomer with the accelerator (Dimethyl p-toluidine 0.03%) was mixed. When viewing a homogeneous mixture, the photoactivator (0.3% camphoroquinone) was added. Micrometric silicon dioxide (56%) was added to finish with nanometric silicon dioxide (2%). After obtaining a homogeneous mixture, it was stored in an amber bottle, labeled with the number and date of preparation mixture. The use of less than 56% of micrometric silicon dioxide is not working.

Example 2: Determination of Hardening Time

Figure 10:
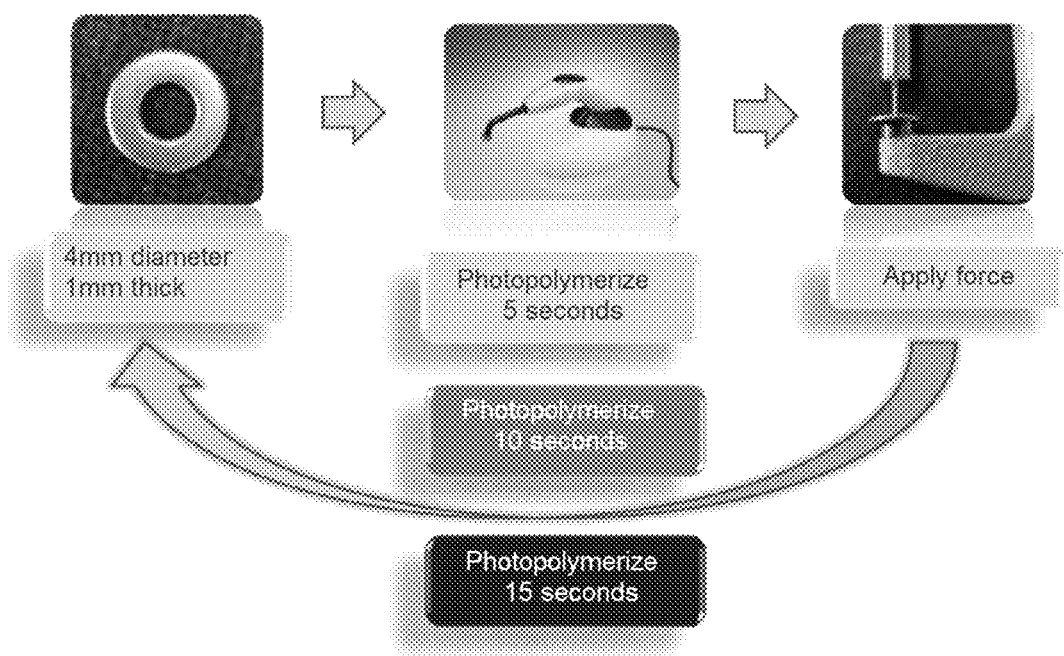
FIG. 10 is a diagram describing the method for determining the curing time.
Figure 11:
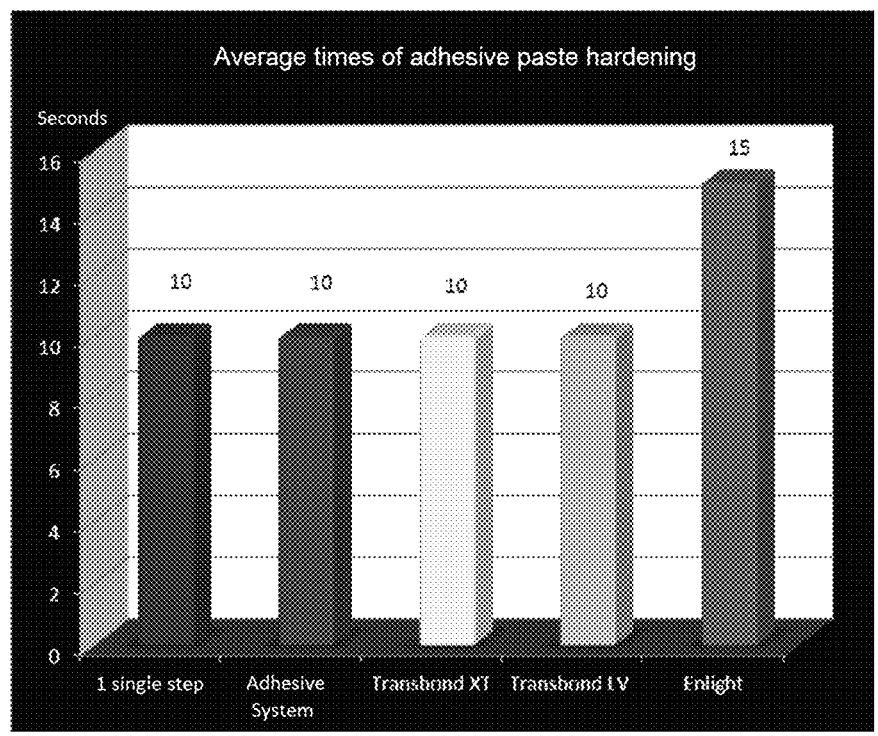
FIG. 11 is a graph showing the average curing time of orthodontic adhesive (paste).
Figure 12:
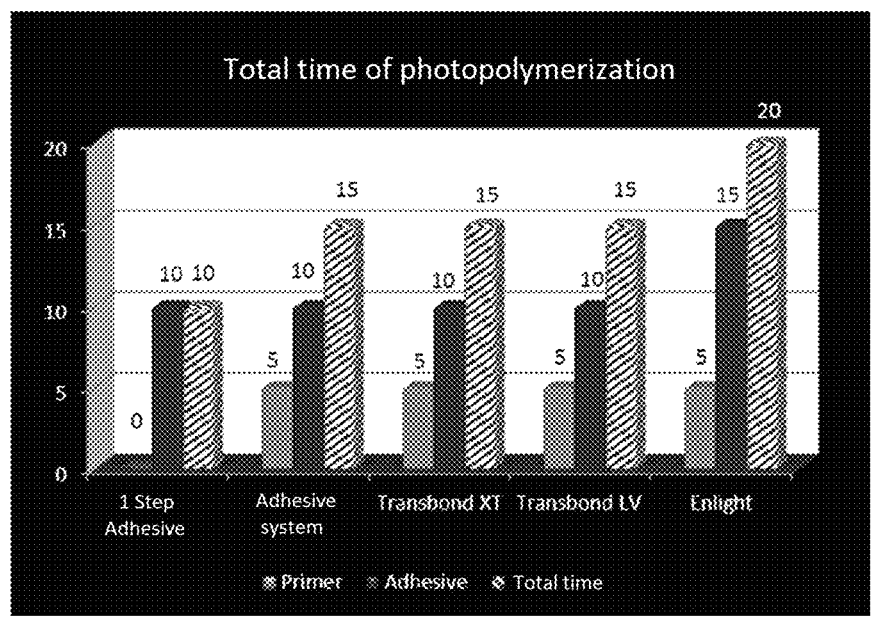
FIG. 12 is a graph showing the average total cure time of orthodontic adhesives (adhesive systems).

The hardening time of the adhesive was determined by placing a drop of adhesive in a stainless steel mold of 4 mm in diameter and 1 mm of thick with teflon spatula until rasar it; It was irradiated with a light source (previously assessed as to irradiation: 600 mW/cm$^2$) for 5 seconds. Subsequently, a perpendicular force was applied to penetrate the adhesive using a micrometer screw with a sharps attachment. If the adhesive was not yet hardened, another drop of adhesive was placed in the mold and was photopolymerized for 10 seconds, the procedure of indentation was performed. The total procedure is repeated until immersed hardening material into the mold. FIG. 10 shows the test sequence. The hardening time of each adhesive mixture is shown in the graph of FIG. 11 and averages in the graph of FIG. 12.

Example 3: Determination of Peel Strength

To determine the peel strength, elastic modulus and maximum stress supported by the adhesive were calculated, for which was carried out the following protocol:

Human teeth were used for each group numbered as (1) Adhesive of the invention, 2) Adhesive A, 3) Adhesive C and 4) Adhesive B. The teeth were washed by removing the periodontal ligament, were stored in water and chilled at 5±2° C. until use.

The teeth were cut 5 mm apical of the line of cement-enamel junction (below the anatomical crown) to locate the anatomical center line at the center of the cylinder (sample holder). Prophylaxis was performed on the buccal surface of the teeth with rubber cup and fluoride-free prophylaxis paste, washed with pressurized water and dried with compressed air, free of oil.

Teeth carried adhesives of the invention (experimental) were wiped with phosphoric acid diluted in water to 37%, with a micro-brush on the adhesion area for 15 seconds; washed and dried for 20 seconds, the adhesive was applied to the base of the brace and on the surface of the treated enamel with etchant acid and using a clamp holder brace, placed at the center of the clinical crown, pressing the center of the brace to remove excess of adhesive with a scanning, for immediately photopolymerize.

For commercial adhesives, manufacturer's instructions were followed. The teeth of the adhesive system of the invention and of the commercials A and B were rubbed with phosphoric acid 37% with a micro-brush on the adhesion area for 15 seconds; washed and dried for 20 seconds; a primer homogeneous layer was applied and polymerized 5 seconds. For the teeth of the group C, a homogeneous layer of primer was applied following the manufacturer's instructions, after applying the primer, was blown with oil-free air for 5 seconds and photopolymerized focusing the light from the lamp for 10 seconds.

For placing the appliances, the adhesive was applied on the brace and for the one-step adhesive of the invention (experimental) it was also applied on the tooth surface and using holder clamp brace, was placed at the center of the anatomical crown tooth, pressing the center of the brace to remove the excess of adhesive with a scanning, for commercial adhesives, was photopolymerized following the manufacturer's instructions, and for the experimental 10 seconds as determined in the test "determination of the hardening time" (tilting the lamp to radiate to the four sides of the brace).

Figure 13:
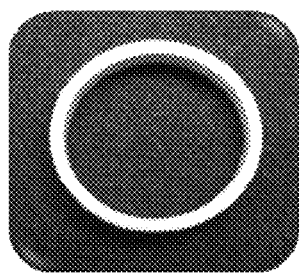
FIG. 13 shows a photograph of a PVC mold.

Considering the procedure of the technical specification ISO 11405[14], PVC molds of 28 mm external diameter and 10 mm in height (FIG. 13) were obtained. The teeth with braces attached were placed in the center of the PVC ring; these were filled with self-polymerizing acrylic mixed in volumetric ratio 3:1 of polymer-monomer according to the manufacturer's instructions. They were allowed to polymerize at ambient conditions to obtain test specimens. The samples were labeled and stored for 24 hours at 37±1° C. in an oven.

Figure 14:
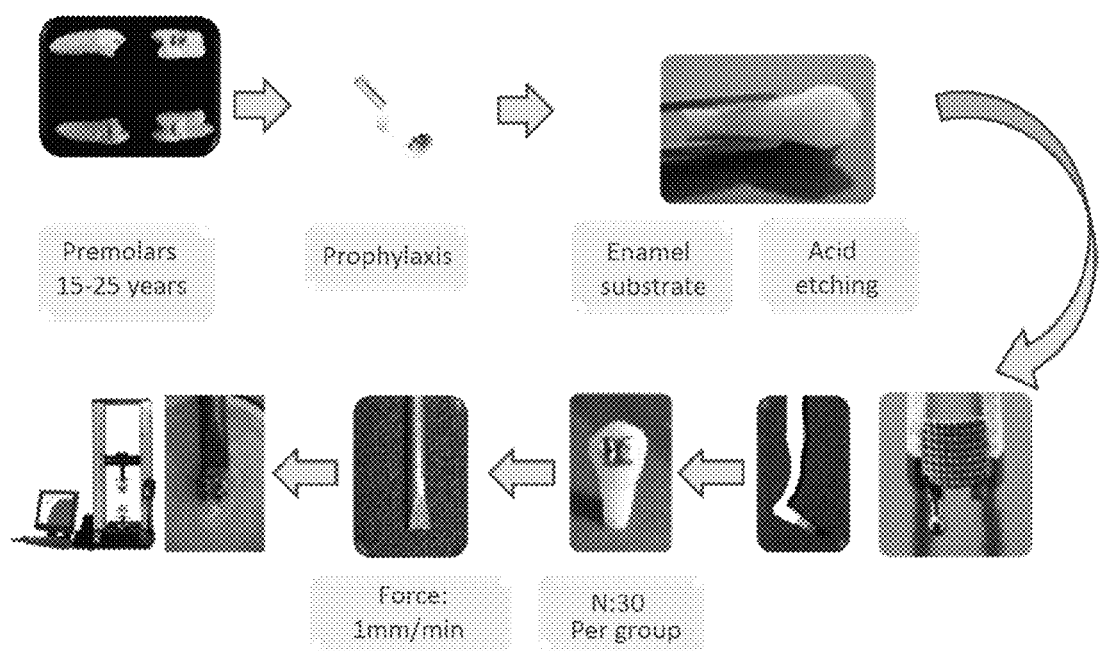
FIG. 14 is a diagram describing the sequence of steps to evaluate peel strength.

The PVC cylinders were installed in a holder on the universal machine of mechanical testing. The tip of the applicator was placed parallel to the brace base and a loading rate of 1 mm/min was applied. Force values for each sample were recorded. In FIG. 14 the sequence of steps to evaluate the peel strength are illustrated.

The elastic modulus (E) and maximum stress (R) supported by the adhesive were calculated using the following equations, the results are shown in graphs 3 and 4 (FIGS. 15 and 16).

$$E = \frac{\sigma_{in\ the\ elastic\ zone}}{\varepsilon_{in\ the\ elastic\ zone}}$$

Where $\sigma$ is stress and $\varepsilon$ is the strain $$R = \frac{Force_{maximum}}{A_{original}}$$

Where $A_{original}$ is the bond area of the brace (mesh).

In graph 3, FIG. 15 shows that the adhesive of the invention has similar values at the 3 commercial ones. Non adhesive presented statistically significant difference when tested with substrates of tooth enamel and metal braces.

In graph 4, FIG. 16 shows that the adhesive of the invention is provided to lower elastic modulus, which represents the most important difference compared to the three commercial ones during this evaluation stage. Being a less rigid material, have better performance in clinical use allowing dissipate forces applied to the brace, the adhesive will absorb and flex slightly to dissipate it toward to the tooth without breaking. The three commercial ones, at the time of being more rigid (higher value), have the risk of fail when thicker arc is applied.

Example 4: Identification of the Type and Site of ARI[14] Failure

Figure 17:
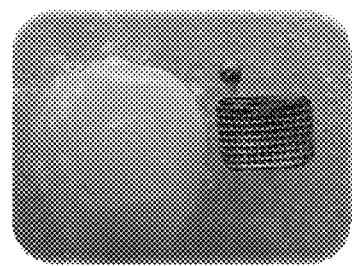
FIG. 17 shows a photograph of a typical image of the fail type 2.

All specimens used to evaluate peel strength were examined using a microscope to determine the type of failure (Table 1 and FIG. 17), adhesive, cohesive or combined.

| ARI index (adhesive remnant index) | |
| --- | --- |
| 0 | Without adhesive on the tooth. |
| 1 | Less than 50% adhesive on the tooth. |
| 2 | More than 50% of adhesive on the tooth. (FIG. 17) |
| 3 | 100% of adhesive on the tooth. |

Figure 18:
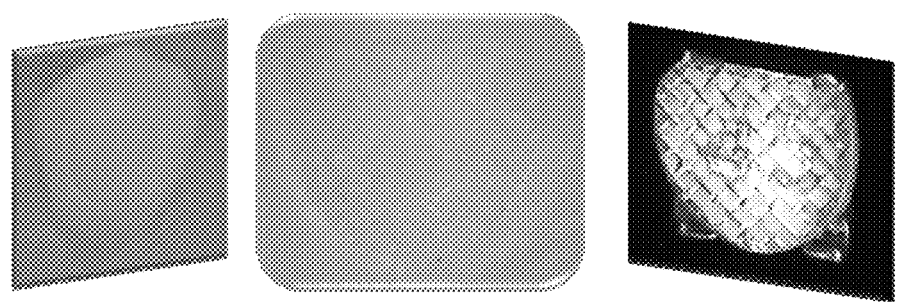
FIG. 18 shows a photograph of a typical image of the tooth and brace after making bond strength test with adhesive of the invention or experimental.
Figure 19:
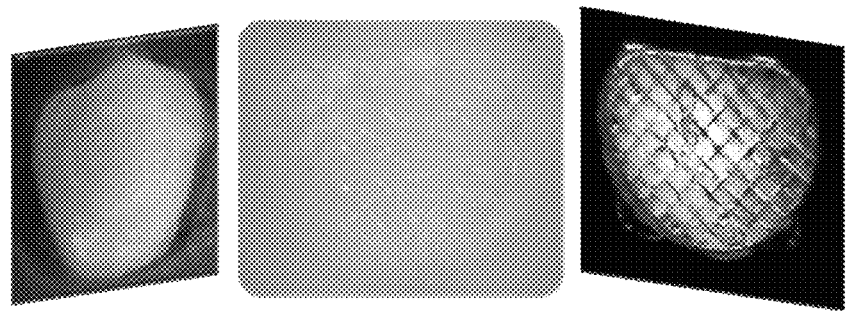
FIG. 19 shows a photograph of a typical image of the tooth and brace after making bond strength test with adhesive system of the invention (experimental).
Figure 20:
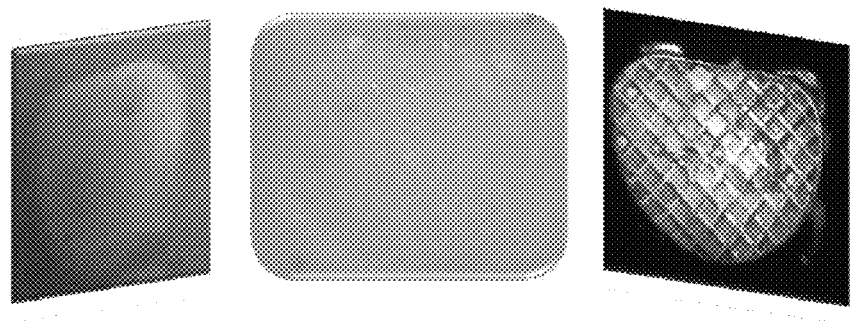
FIG. 20 shows a photograph of a typical image of the tooth and brace after making bond strength test with Adhesive A.
Figure 21:
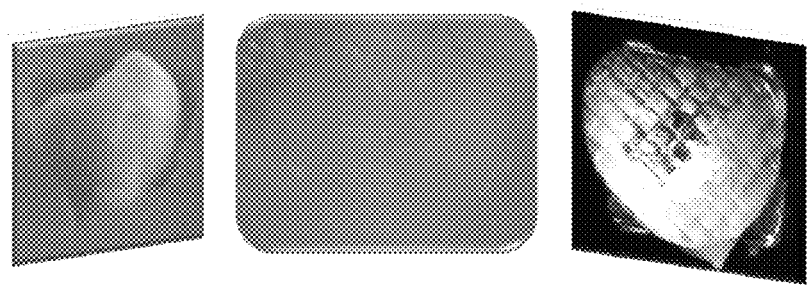
FIG. 21 shows a photograph of a typical image of the tooth and brace after making bond strength test with Adhesive C.
Figure 22:
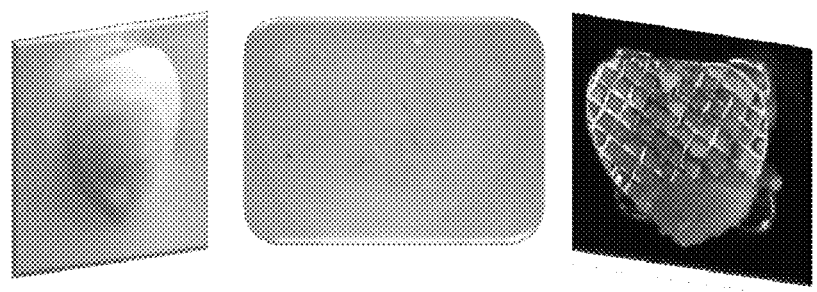
FIG. 22 shows a photograph of a typical image of the tooth and brace after making bond strength test with Adhesive B.

The type and location of failure that presented the one-step adhesive and adhesive system was equal to the commercial Adhesive A (FIGS. 18-20) ARI 3, A: who allowed 100% of adhesive to remain on the enamel surface, ensuring the integrity of the enamel rods avoiding detaching when removing the appliance at the end of treatment. Unlike the other two commercial ones, due to that Adhesive C (FIG. 21) provides ARI 1, Adhesive: less than 50% of adhesive on the enamel and Adhesive B (FIG. 22) ARI 2, Adhesive: presented more than 50% of adhesive on the tooth.

The three commercial adhesives despite of being Bis-GMA based have different behavior, being the least desirable the adhesive with Transbond Supreme LV, as this when perform the detaching of the braces remain only less than 50% of the adhesive on the tooth, we can infer that there is risk of damaging the enamel with possible rods landslides, which can be reflected in sensitivity in the patient.

Example 5: Determination of the Sorption and Solubility[15]

Figure 23:
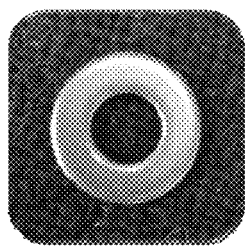
FIG. 23 shows a photograph of a mold for sorption and solubility.

Each group of specimens were prepared using a stainless steel mold of 4.43 mm in diameter and 1.5 mm thick (FIG. 23). A drop of adhesive was placed to the center of the mold.

A photopolymerizer lamp was used, previously assessing their performance in terms of irradiance (600 mW/cm²). The tip of the photopolymerizer lamp was placed on the center of the adhesive for 10 seconds, except for Adhesive B who required 15 seconds. Once polymerized, were placed within the desiccator with silica and placed within the controlled temperature chamber at 37±1° C. The silica was previously dried for 5 hours at 130° C. After 24 hours, the samples were weighed on an analytical balance with an accuracy of ±0.2 mg, repeating this cycle until a constant mass was obtained, i.e. until the missing mass of each sample was not more than 0.2 mg in a 24 hour period. This measurement was reported as $M_1$.

Once stabilized, the specimens were immersed individually in sealed containers in two types of water: Group 1) demineralized water (pH 7.7) and group 2) double distilled water (pH 6.8)[18-28]. The containers were stored at 37° C. for 7 days in a temperature-controlled chamber. After this time, the specimens were removed, dried with paper, stirred in air for 15 seconds and once after one minute from being removed from the water, they were weighed to obtain (M2).

Figure 24:
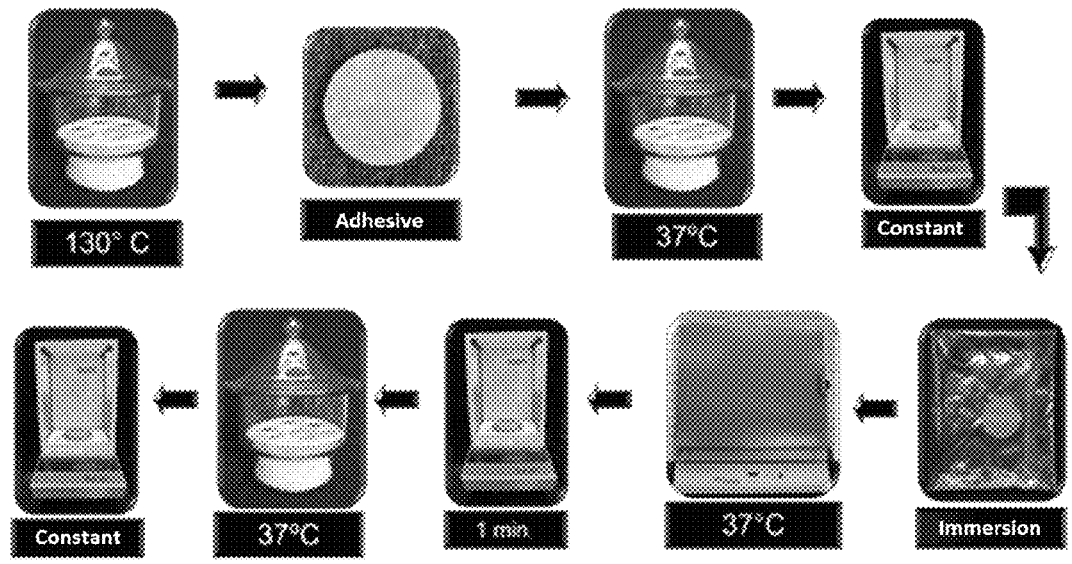
FIG. 24 is a diagram describing the method for calculating sorption and solubility

The specimens were placed in a desiccator at 37° C., they weighed until the weight loss was not more than 0.2 mg; It was reported as $M_3$ (FIG. 24).

The diameter and thickness of each specimen was measured from the center toward the circumference and four orthogonal dots placed at the same distance to calculate the volume in cubic millimeters:

$$V = \frac{\Pi D^2 h}{4}$$

where:
V=volume of the specimen.
D=diameter of the specimen.
h=thickness of the specimen.

To calculate the water sorption, S, expressed in $\mu g/cm^3$, the following formula was used:

$$S = \frac{M_2 - M_1}{V}$$

where:
$M_1$=the sample weight after the first drying.
$M_2$=the weight of the sample after 7 days of immersion in water.

For solubility, $Ws_1$ in $\mu g/cm^3$, for each of the specimens the following equation was used:

$$Ws_1 = \frac{M_1 - M_3}{V}$$

where:
$M_1$=the sample weight after the first drying.
$M_3$=the sample weight after the second drying.

Figure 25:
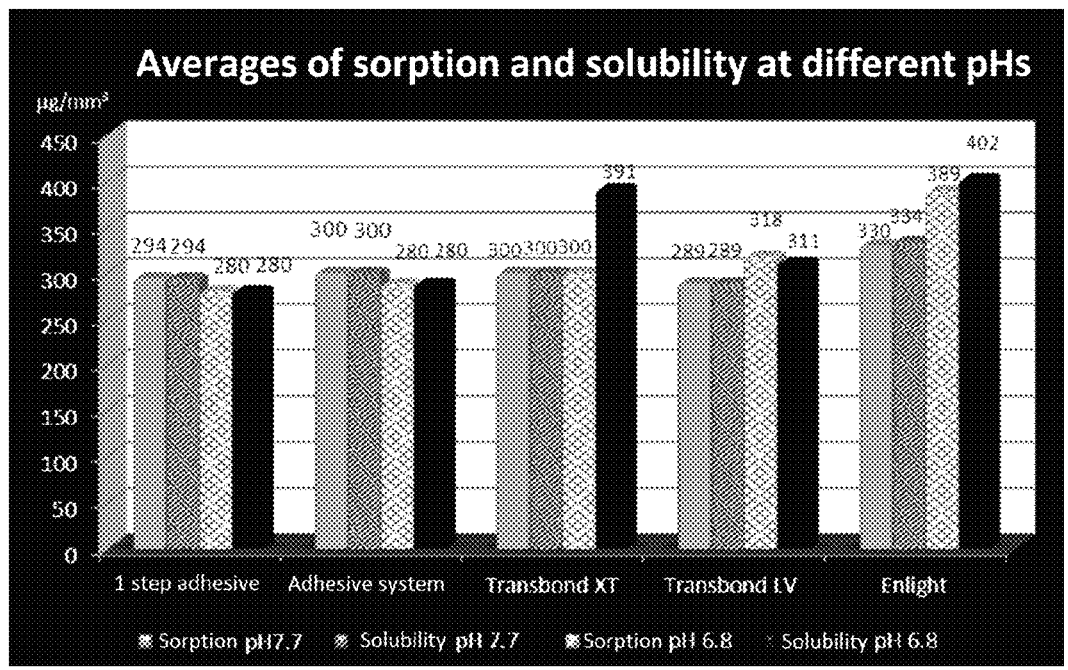
FIG. 25 is a graph showing the average sorption and solubility of pastes at different pH.
Figure 26:
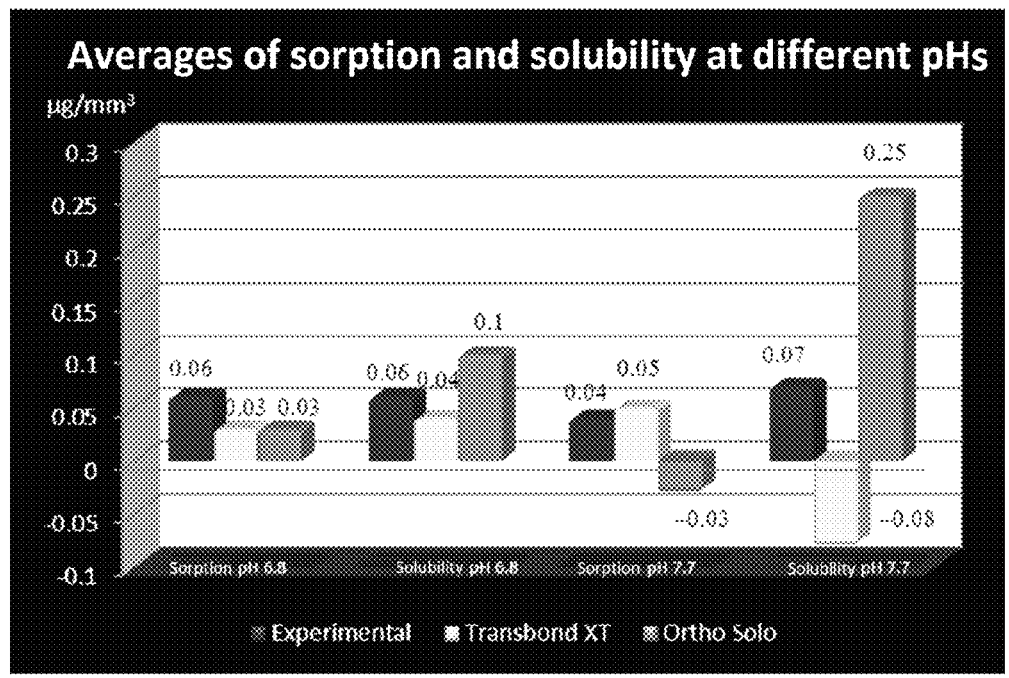
FIG. 26 is a graph showing the sorption and solubility of primers at different pH (Primers).

In graph 5 and 6 (FIGS. 25 and 26) the results obtained are shown; This graph shows that the experimental adhesive as well as Adhesive C, are those presented lower sorption and solubility when tested at basic pH (7.7) and both were stable; the experimental presented the best behavior immersed in acid pH (6.8) so it can be inferred that the trimethylolpropane trimethacrylate is more resistant to an acidic aqueous medium.

With these results, is expected that the experimental adhesive presents the best outperform, than the commercial ones when clinically tested because they may be used in any type of patient (regardless of salivary pH).

Example 6: Determination of Fluidity[15]

Figure 27:
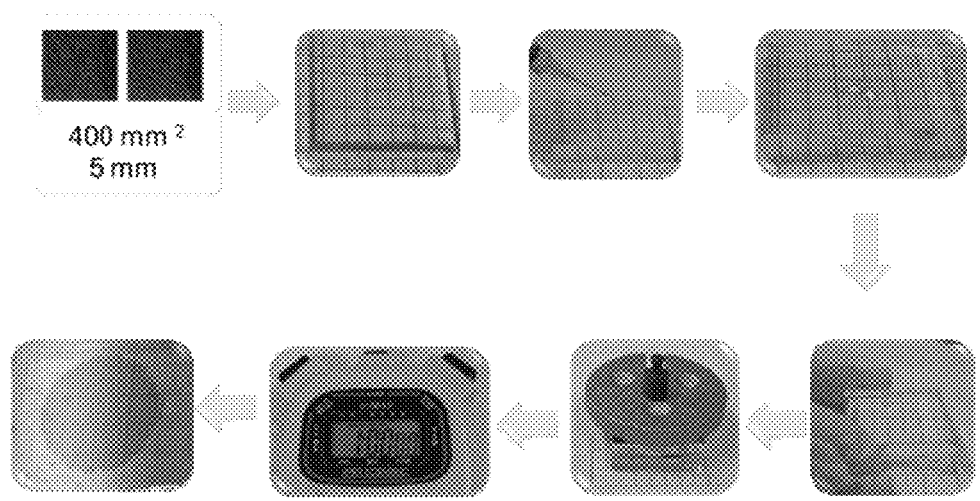
FIG. 27 is a diagram describing the method of measuring flow.

To evaluate the fluidity of materials, a sheet of graph paper was placed under a glass plate (30 mm wide×30 mm long and 5 mm thick); 0.5 mL of adhesive were placed on the glass plate; immediately afterwards, the adhesive was covered with another glass plate of the same dimensions, and placing on them and at the center two dumbbells so that give a total weight of 120 g on the adhesive. They were placed inside the filter chamber to the light for 1 minute because mixtures and commercial adhesives are photopolymerizables; after this time, it was measured on the graph paper, the smallest diameter and the largest diameter of each sample. FIG. 27 shows the sequence of steps to measure fluidity. The average of the two measurements of the diameter was reported to calculate the area of each sample using the formula.

$$A = \pi r^2$$

Figure 28:
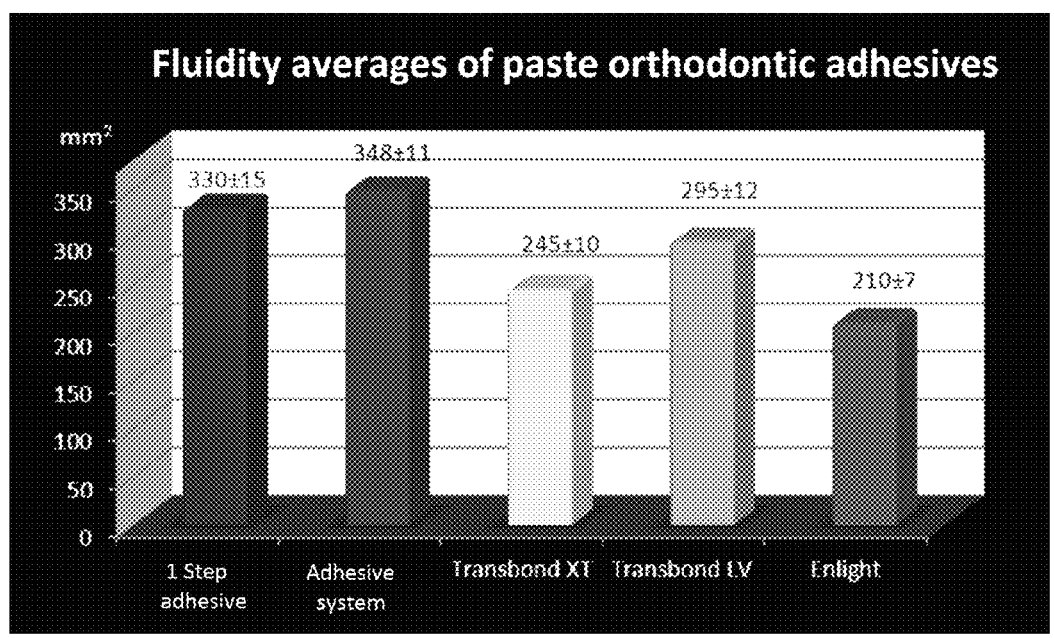
FIG. 28 is a graph showing the average fluidity of orthodontic adhesives (in paste).
Figure 29:
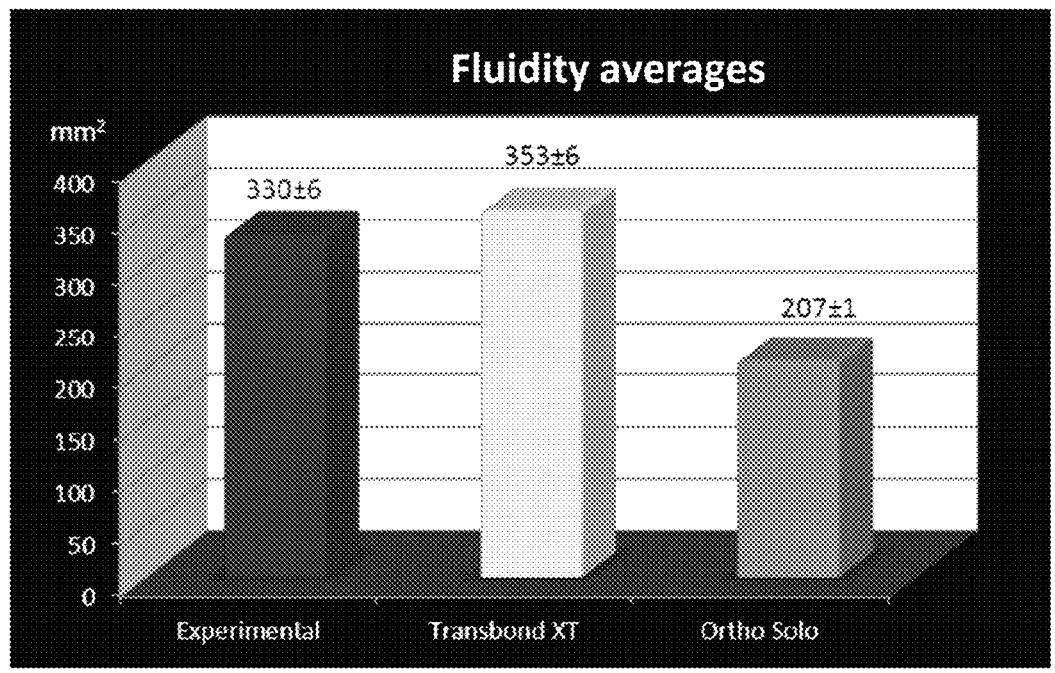
FIG. 29 is a graph showing the average fluidity of orthodontic adhesives (in primer).

The fluidity results are shown in graphs 7 and 8 (FIGS. 28 and 29), where the it can be observed that the more fluid adhesive is the experimental one (330±15 $mm^2$); Adhesive C presented 295±12 $mm^2$ which means that both can penetrate more easily into the micro-downs created by the acid etching on enamel surface and in the mesh or withholdings the base of the attachments, Adhesives A and B presented less fluently.

Example 7: Determination of Film Thickness

Figure 30:
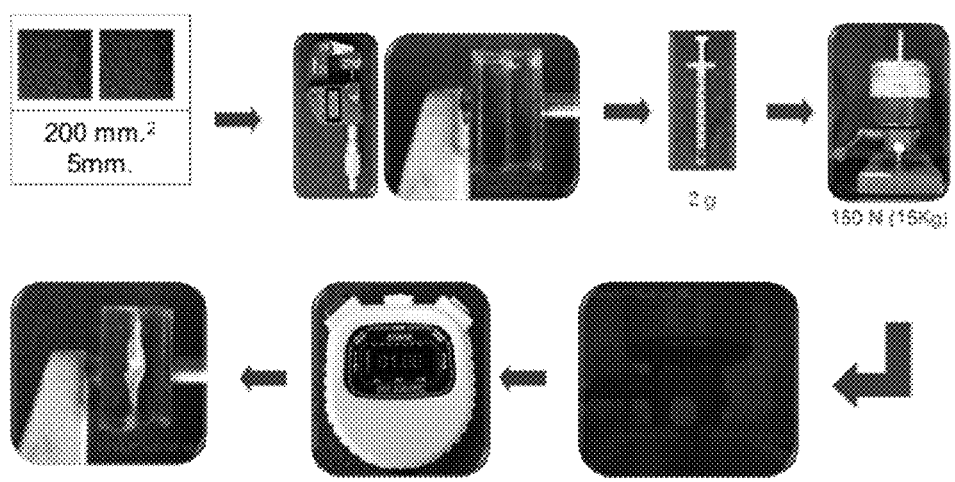
FIG. 30 is a scheme describing the procedure for determining film thickness.

The test was performed inside of an orange chamber to filter the light and prevent the photopolimerization of the adhesives. Two square glass plates were used, placing one upon another, measured with the micrometer screw; reporting this as reading A. The upper glass was removed, 0.2 g of adhesive were placed in the center of the plate glass, the upper glass was placed again in the same position as the first measurement was made. Were placed entered beneath the loading device, previously calibrated and 150 N (15 Kg) were applied. After 10 minutes, the load was removed and measured again, this measured recorded as reading B. FIG. 30 shows the procedure.

To report the film thickness, the difference of the thickness of the plates were scored without the adhesive film.

$$E = (\text{Reading } B - \text{Reading } A).$$

Figure 31:
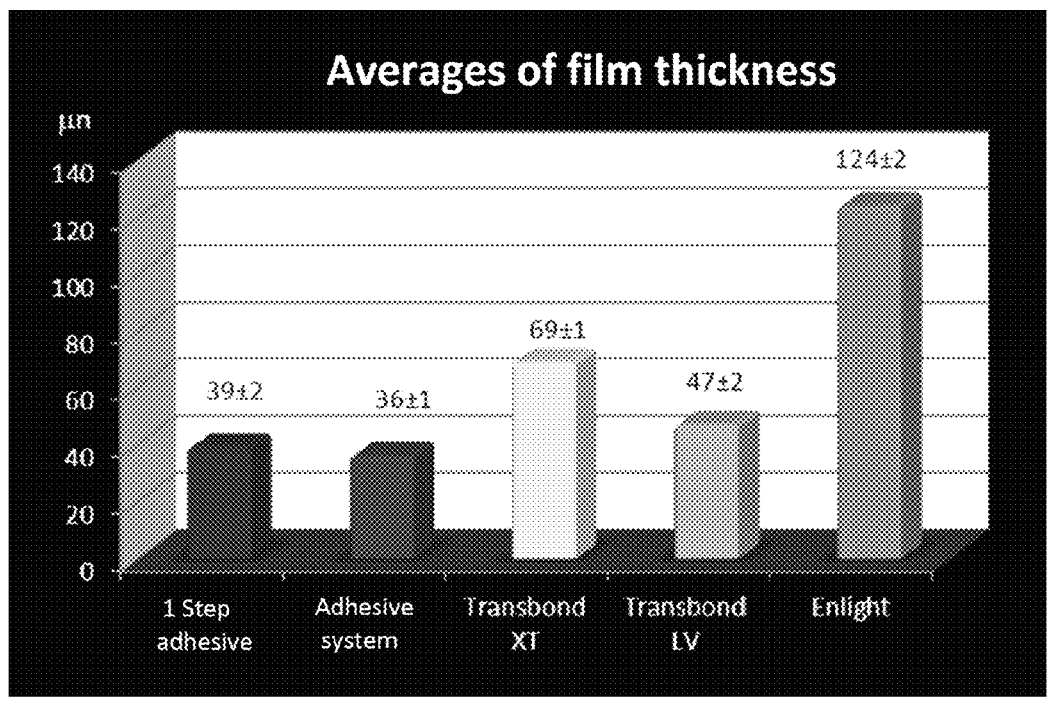
FIG. 31 is a graph showing the average film thickness of orthodontic adhesives

The results are shown in graph 9 (FIG. 31). This graph shows the average film thickness; the experimental adhesive that is of the invention, shows the thinner thickness (39±2 $\mu m$) similar to Adhesive C (47±2 $\mu m$). The adhesive of the invention allows to maintain the brace base as close as possible to the enamel surface, with which is respected the system requirements, and exhibits less thickness in the periphery of the brace when the adhesive also polymerizes, helping sorption and solubility decrease.

Example 8: Determination of Storage Stability

After the mixture was left to stand for 24 hours and observed with the naked eye to determine whether continued homogeneous. A drop was placed inside a stainless steel mold (1±0.2 mm thick 4±0.2 mm internal diameter); and placing on a black surface, a digital photograph was taken; this observation was performed every 60 days to compare for changes in color.

To determine if the experimental adhesive is stable to remain stored, digital photographs were taken to the amber bottles that contained at a room temperature with the sole intent of determining whether the phases of the adhesives separated.

New blends were manufactured, photopolymerized and compared with the manufactured 8 months before (photopolymerized immediately after obtained the mixture in April 2012), to determine if the adhesive had presented color change.

FIG. 29A shows that they have not presented apparent change of color. FIG. 29B does not evidence separation after being kept standing for 8 months.

Example 9: Determination of Thermal Stability: Thermal Gravimetric Analysis

To determine the presence of residual monomer, studies of thermogravimetric were made. Stainless steel molds (1 mm thick×4 mm diameter) previously washed with acetone were used. To obtain the specimens, molds were filled with each adhesive, they were photopolymerized, assessing previously the lamp regarding irradiance (600 mW/cm2) using a curing radiometer.

Figure 34A:
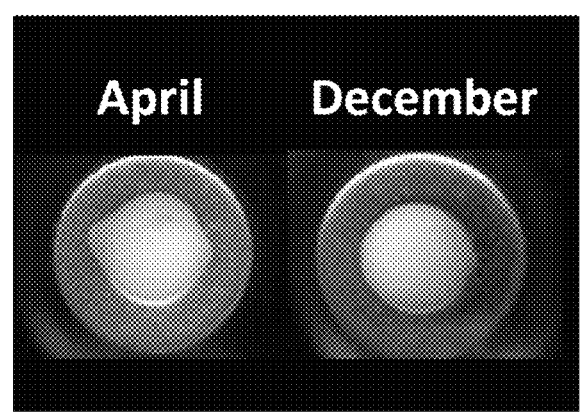
FIG. 34A shows a photograph of the initial image of the adhesive when is photopolymerized, made immediately after mixing in the month, of April, in December, corresponding to the polymerization of the adhesive after 8 months of mixing with what is explained that the color of the adhesive has not been changed since its preparation, i.e. maintains color stability.
Figure 34B:
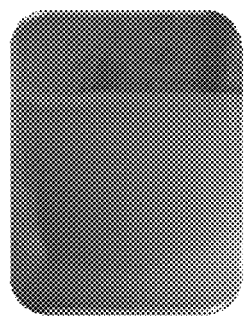
FIG. 34B shows a photograph of the image of the adhesive in resting during the 8 months of the mixture, in which it is observed that there is no phase separation.
Figure 34C:
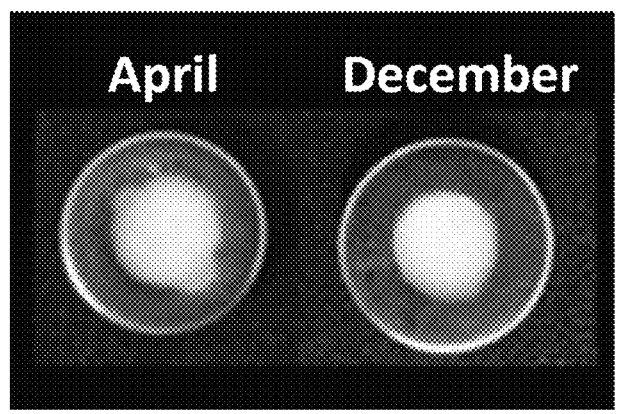
FIG. 34C shows a photograph of the initial image of the paste of the adhesive system when is photopolymerized, made immediately after mixing in the month, of April, in December, corresponding to the polymerization of the adhesive after 8 months of mixing with what is explained that the color of the adhesive has not been changed since its preparation, i.e. maintains color stability.
Figure 34D:
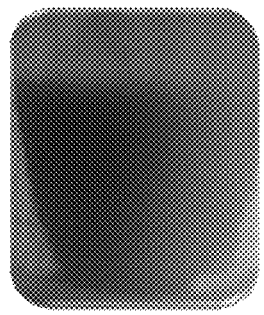
FIG. 34D shows a photograph of the image of the adhesive in resting for 8 months of the mixture in which it is observed that there is no phase separation.

The light incident on the samples of the experimental adhesives or of the invention for 10 seconds (previously determined time in the test of hardening time); commercial adhesives were polymerized according to the manufacturer's instructions: Adhesive A and Adhesive C for 10 seconds and adhesive B for 15 seconds. Once the material was photopolymerized, they were demolded (FIG. 34A to 34C).

Figures 35, 36:
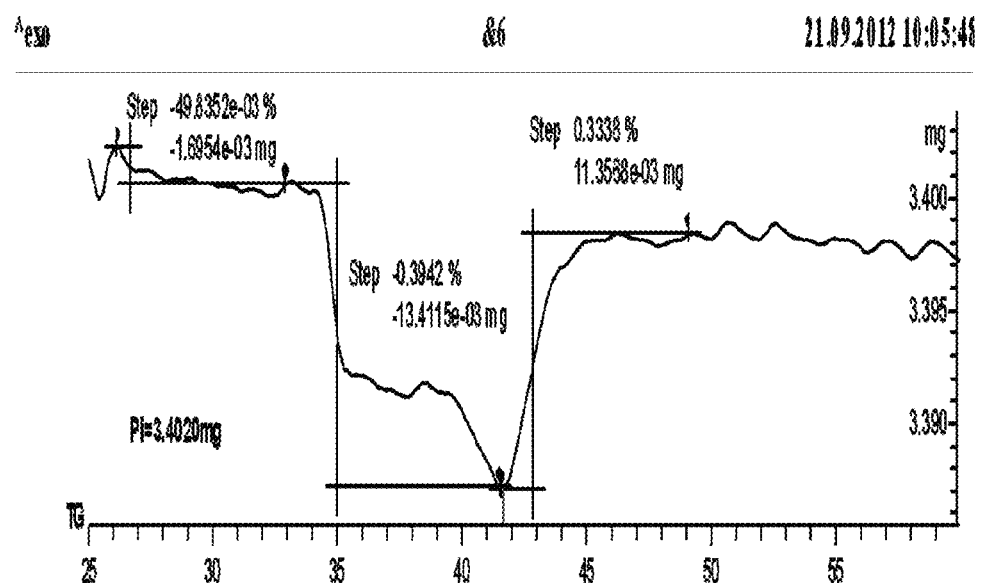
FIG. 35 is a table showing the percentage loss of mass of the orthodontic adhesives subjected to thermogravimetry.
FIG. 36 is a graph showing thermogravimetric performance of the adhesive of one-step of the invention.
Figure 37:
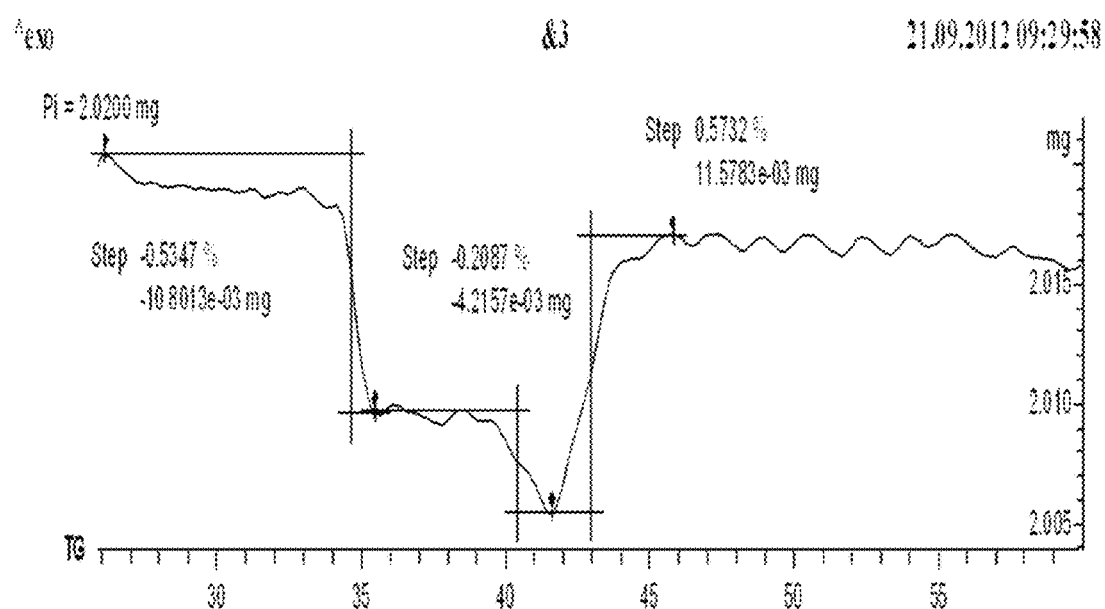
FIG. 37 is a graph showing thermogravimetric performance of the adhesive of the adhesive system of the invention.

Once the material was demoulded a mortar and pestle of agate was used to fragment the material. Each sample was weighed in alumina cells 70 µL (open). The test was performed in ambient atmosphere, in intervals of 25 to 60° C., with heating rate of 5° C./min. The percentage mass loss was determined at different temperatures. Table 2 shows the results obtained (FIG. 35), there was no loss of mass or was negligible so it was concluded that all adhesives have stability when they were heated from 25 to 60° C. Graph 10 (FIG. 36) has a typical thermogram of this study and corresponds to the thermogram presenting the one-step adhesive of the invention. Graph 11 (FIG. 37) presents a typical thermogram of this study and corresponds to the thermogram presenting the adhesive system of the invention.

Therefore, it will be apparent to one skilled in the art that the embodiments of the present invention are only illustrative but not limitative of the present invention, as many changes are possible consideration in their details, but without leaving the scope of the invention.

Even when they have shown and described certain embodiments of the invention, it should be emphasized that many modifications are possible to it, but those changes do not represent a departure from the true scope of the invention. Therefore, the present invention should not be considered as restricted except as provided in the prior art and by the scope of the appended claims.

REFERENCES

1. Ríos Hernández, M, et. al. Evaluación toxicológica in vitro de materiales poliméricos de restauración dental compuestos por Bis-GMA. Anuario Toxicología 2001 Instituto Nacional de Oncología y Radiobiología; 1(1): 65-72.
2. Dimitrios Kloukos, Nikolaos Pandis, Theodore Eliades Bisphenol-A and residual monomer leaching from orthodontic adhesive resins and polycarbonate brackets: A systematic review. American Journal of Orthodontics and Dentofacial Orthopedics, Volume 143, Issue 4, Supplement, April 2013, Pages S104-S112.
3. Söderholm K J, Mariotti A. BIS-GMA-based resins in dentistry: are they safe?. J Am Dent Assoc. 1999 February; 130(2):201-9.
4. Olea N, Pulgar R, Pérez P, Olea-Serrano F, Rivas A, Novillo-Fertrell A, Pedraza V, Soto A M, Sonnenschein C. Estrogenicity of resin-based composites and sealants used in dentistry. Environ Health Perspect. 1996 March; 104 (3):298-305.
5. Fung E Y, Ewoldsen N O, St Germain H A Jr, Marx D B, Miaw C L, Siew C, Chou H N, Gruninger S E, Meyer D M. Pharmacokinetics of bisphenol A released from a dental sealant. J Am Dent Assoc. 2000 January; 131(1): 51-8.
6. Fleisch A F, Sheffield P E, Chinn C, Edelstein B L, Landrigan P J. Bisphenol A and related compounds in dental materials. Pediatrics. 2010 October; 126(4):760-8. doi: 10.1542/peds.2009-2693. Epub 2010 Sep. 6.
7. Schmalz G, Preiss A, Arenholt-Bindslev D. Bisphenol-A content of resin monomers and related degradation products. Clin Oral Investig. 1999 September; 3(3):114-9.
8. Dimitrios Kloukos, Nikolaos Pandis, and Theodore Eliades. Bisphenol-A and residual monomer leaching from orthodontic adhesive resins and polycarbonate brackets: A systematic review. Am J Orthod Dentofacial Orthop 143(4 Suppl):S104-S112.e2 (2013).
9. Adobes-Martín M. Eficacia de adhesivos autograbantes en el cementado de brackets. Autores: Localización: Revista Española de Ortodoncia, ISSN 0210-0576, Vol. 34, No. 1, 2004, págs. 29-34.
10. J R Reynolds. A review of direct orthodontic bonding British journal of orthodontics 1975; 171.
11. López-Palacios Eira. Propiedades físicas de 4 adhesivos para brackets: estudio comparativo. International Association for Dental Research, IADR Reunión anual de la División Mexicana, Acapulco, México Junio 10, 2008.
12. 3M Unitek product catalog.
13. ORMCO Corporation product catalog.
14. Technical Specification the International Organization Standardization ISO/TS 11405: Second edition 2003 Feb. 1 Dental materials. Testing of adhesion to tooth structure Terms and definitions 3.5. Indice ARI.
15. Artun J., Bergland Am J Orthod Dentofacial Orthop 1995.
16. Technical Specification the International Organization Standardization ISO/TS 6876: 1996, 7.6. For endodontic filling materials.
17. Technical Specification the International Organization Standardization ISO/TS 4049: 1998 Resin-Based Filling materials.
18. Osorio González, Antonio Bascones Martínez, M. Villaroel Dorrego Alteración del pH salival en pacientes fumadores con enfermedad periodontal Avances en periodoncia e implantología oral 2009; 21 (2): 75-79.
19. Stabholz A, Mann J, Sela M, Steinberg D, Shapira J. Department of Community Dentistry, "Caries experience, Periodontal treatment needs, salivary pH and Counts in a Preadolescent Down's Syndrome population". Spec. Care Dentist. 1991; 11; (5): 203-208.
20. Vaca M J, Ceballos L, Fuentes M Y, Osorio R, Toledano M, García-Godoy F. Sorción y solubilidad de materiales formulados con resina. Avances en odontoestomatología 2003. Vol. 19 (6): 283-289.
21. Bernardi M G, Reis A, Loguercio A D, Kehrig R, Leite M F, Nicolau J. Study of the Buffering Capacity, pH and Salivary Rate in type 2 well-controlled and poorly controlled diabetic patients. Oral Health Prev Dent. 2007; 5(1): 73-78.
22. Koparal E, Eronat C, Eronat N. In vivo assessment of dental plaque pH changes in children after ingestion of snack foods. ASDC J Dent Child. 1998; 65 (6): 478-83.
23. Sixto García Linares1, Francis Bravo Castañola2, Jocelyn Ayala Luis3, Guadalupe Bardales Cuzquén3 Total saliva pH in patients with periodontal disease of UNMSM Dental Faculty Periodontal Service Odontol. Sanmarquina 2008; 11(1): 19-21.
24. Eggert F., Drewell L., Bigelow J., The pH of gingival crevices and periodontal pockets in children, teenagers and adults Oral biology 1991; 36(3): 295-303.
25. Galgut P., The relevance of pH to gingivitis and periodontitis, Journal Academy periodontology 2001; 3(3).
26. Romero H M, Hernández Y. Modificaciones del pH y flujo salival con el uso de aparatología funcional tipo Bimbler. Revista Latinoamericana de Ortodoncia y Odontopediatria "Ortodoncia.ws edición electrónica Marzo 2009.
27. Coudray M, Baehni P, Lang R. Effects of orthodontic bans on microbiologic and clinical parameters. Am J. Orthod Dentofac Orthop. 1990; 97: 213-218.
28. Zárate A, Leyva E, Franco F. Determinación de pH y proteínas totales en saliva en pacientes con y sin aparatología ortodóncica fija (estudio piloto). Revista Odontológica Mexicana. 2004; 8 (3): 59-63.
29. Technical Specification The International Organization Standardization ISO/TS 3696:1987. Water for analytical laboratory use.
30. Technical Specification the International Organization Standardization ISO/TS 9917:1991, Dental Water Cements.
31. Technical Specification The International Organization Standardization ISO/TS 3696:1987. Water for analytical laboratory use.
32. Dumitrascu C. Borcia B. Determining the contact angle between liquids and cylindrical surfaces. Journal of Colloid and Int Sci. 2006; 294: 418-42.
33. Inaba H, Sato K. A measurement of interfacial tension between tetradecane and ethylene glycol water solution by means of the pendant drop method. Fluid Phase Equilibria. 1996; 125: 159-168.

The invention claimed is:
1. An orthodontic adhesive in paste comprising two phases:
a) an organic phase consisting of: a monomer trimethylolpropane trimethacrylate at a concentration of 40.67% w/w, a camphorquinone at a concentration of 0.3% as a photoinitiator; a dimethyl p-toluidine at a concentration of 0.03% as an accelerator; and
b) an inorganic phase comprising: a silanized silicon dioxide at a concentration of 2% w/w with a maximum particle size of 16 nm and silanized silicon dioxide at a concentration of 57% w/w with a maximum particle size of 325 microns.

2. An orthodontic adhesive comprising:
an organic phase consisting of: a monomer trimethylolpropane trimethacrylate at a concentration of 40.67% w/w, a camphorquinone at a concentration of 0.3% as a photoinitiator: a dimethyl p-toluidine at a concentration of 0.03% as an accelerator;
an inorganic phase comprising: a silanized silicon dioxide at a concentration of 2% w/w with a maximum particle size of 16 nm and a silanized silicon dioxide at a concentration of 57% w/w with a maximum particle size of 325 microns;
an elastic modulus of 30 MPa, thus allowing adequate transmission of forces to the tooth, generated by orthodontic appliances;
adhesion to both the base of the attachments and the enamel, so it does not damage the enamel;
a minimal sorption of 294 mg/mm3 at both pH 7.7 and pH 6.8;
a minimal solubility of 280 mg/mm3 at both pH 7.7 and pH 6.8, demonstrating its stability to pH changes and resistance to the oral acid pH; a
fluidity of 330±15 mm2, so that its viscosity is low and allows easily penetrate both in micro-downs enamel created by acid etching effect and the base of the attachments; and
a film thickness of 39±2 μm,
wherein it hardens within 10 seconds without requiring a primer.

3. An orthodontic adhesive comprising:
an organic phase consisting of: a monomer trimethylolpropane trimethacrylate at a concentration of 40.67% w/w, a camphorquinone at a concentration of 0.3% as a photoinitiator: a dimethyl p-toluidine at a concentration of 0.03% as an accelerator:
an inorganic phase comprising: a silanized silicon dioxide at a concentration of 2% w/w with a maximum particle size of 16 nm and a silanized silicon dioxide at a concentration of 57% w/w with a maximum particle size of 325 microns; and
an adhesion strength of 9.5±1.5 MPa so that it supports the tensile and torsional stresses from the movements generated by the orthodontical appliances;
wherein it is photopolymerizable;
wherein it is stable to stand at 21±1° C.;
wherein it is stable to temperature changes ranging from 25 to 60° C.; and
wherein it is stable at oral temperatures and temperature changes ranging from 5 to 55° C.

4. A primer orthodontic characterized by having two phases:
a. an organic phase consisting of a monomer trimethylolpropane trimethacrylate at a concentration of 83.67% w/w, an isopropyl alcohol at a concentration of 10% as a solvent, a camphorquinone at a concentration of 0.3% as a photoinitiator; a dimethyl p-toluidine at a concentration 0.03% as an accelerator;
b. an inorganic phase consisting of: silanized silicon dioxide at a concentration of 6% with a maximum particle size of 16 nm.

5. An orthodontic slurry comprising two phases:
a. an organic phase comprising:
monomer: Trimethylolpropane trimethacrylate at a concentration of 40.67% w/w,
a photoinitiator: camphorquinone at a concentration of 0.3%,
an accelerator: dimethyl p-toluidine at a concentration of 0.03%;
b. an inorganic phase consisting of:
silanized silicon dioxide at a concentration of 3% with a maximum particle size of 16 nm and silanized silicon dioxide at a concentration of 56% with a maximum particle size of 325 microns.

6. A kit comprising an adhesive system comprising:
a. the orthodontic primer of claim 4 formulated in a liquid in amber glass bottle with dropper, b. a liquid etchant acid in amber glass bottle with dropper, c. a slurry in amber glass syringe with dispensing nozzles for its application.

7. An adhesive system constituted by the primer of claim 4, with a slurry, wherein:
   a. it is adhered to a substrate of human dental enamel and orthodontic metal attachments, has a resistance of 6.5±1 MPa sufficient to support the orthodontic biomechanics, whereby there is no detachment of enamel rods when detaching such adhesives;
   b. comprises an elastic modulus of 34 MPa, allowing the orthodontic adhesive in operation, to dissipate the force and transmit such force to the tooth to achieve tooth movement without failure;
   the slurry comprising two phases:
   a. an organic phase comprising:
      monomer: Trimethylolpropane trimethacrylate at a concentration of 40.67% w/w,
      a photoinitiator: camphorquinone at a concentration of 0.3%,
      an accelerator: dimethyl p-toluidine at a concentration of 0.03%;
   b. an inorganic phase consisting of:
      silanized silicon dioxide at a concentration of 3% with a maximum particle size of 16 nm and silanized silicon dioxide at a concentration of 56% with a maximum particle size of 325 microns.

8. A method for obtaining the primer of claim 4, comprising:
   a. mixing on an illuminated light security chamber to prevent photopolymerization, the monomer trimethylolpropane trimethacrylate (TMPTMA) with the initiator camphorquinone at a concentration of 0.3%;
   b. adding, when viewing a homogenous mixture, the photo-activator dimethyl p-toluidine at a concentration of 0.03%;
   c. then adding the nanometric silanized silicon dioxide, dissolved in isopropyl alcohol at a concentration of 6%,
   d. once the homogeneous mixture is obtained, storing said mixture protected from light.

9. An orthodontic adhesive comprising:
   an organic phase consisting of: a monomer trimethylolpropane trimethacrylate at a concentration of 40.67% w/w, a camphorquinone at a concentration of 0.3% as photoinitiator: a dimethyl p-toluidine at a concentration of 0.03% as an accelerator: and
   an inorganic phase comprising: a silanized silicon dioxide at a concentration of 2% w/w and silanized silicon dioxide at a concentration of 57% w/w,
   wherein the silanized silicon dioxide at a concentration of 2% w/w has a particle size of 16 nm and the silanized silicon dioxide at a concentration of 57% w/w has a particle size of 325 microns.

10. A method to obtain the orthodontic adhesive of claim 9, comprising:
    a. mixing on an illuminated light security chamber to prevent the polymerization of the monomer Trimethylolpropane Trimethacrylate (TMPTMA) with the initiator Camphorquinone at a concentration of 0.3%;
    b. adding, when viewing an homogenous mixture, the photo-activator dimethyl p-toluidine at a concentration of 0.03%;
    c. then incorporating the silicon dioxide having a maximum particle size of 325 microns at a concentration of 57%, and at the end incorporating the silicon dioxide having a maximum particle size of 16 nm at a concentration 2%;
    d. once the homogeneous mixture is obtained, storing said mixture protected from light.

11. The primer orthodontic of claim 4 wherein the silanized silicon dioxide has a particle size of 16 nm.

12. The orthodontic slurry of claim 5 wherein the silanized silicon dioxide at a concentration of 3% has a particle size of 16 nm and the silanized silicon dioxide at a concentration of 56% has a particle size of 325 microns.

* * * * *